United States Patent [19]
Kelleher et al.

[11] Patent Number: 5,994,396
[45] Date of Patent: Nov. 30, 1999

[54] FURANSULFONIC ACID DERIVATIVES AND PHARMACEUTICAL COMPOSITIONS CONTAINING THE SAME

[75] Inventors: Judith A. Kelleher, Fremont; Kirk R. Maples, San Jose; Yong-Kang Zhang, Santa Clara, all of Calif.

[73] Assignee: Centaur Pharmaceuticals, Inc., Sunnyvale, Calif.

[21] Appl. No.: 09/130,347

[22] Filed: Aug. 13, 1998

Related U.S. Application Data

[60] Provisional application No. 60/055,916, Aug. 18, 1997.

[51] Int. Cl.[6] .................... A61K 31/34; C07D 307/64
[52] U.S. Cl. ................ 514/471; 514/236.8; 514/326; 544/152; 544/367; 546/214; 548/315.4; 549/479
[58] Field of Search ............................. 549/479; 514/471

[56] References Cited

U.S. PATENT DOCUMENTS

| | | | |
|---|---|---|---|
| 2,844,573 | 7/1958 | Gaspar et al. | 549/479 |
| 4,195,023 | 3/1980 | Mulvey et al. | 548/210 |
| 4,550,114 | 10/1985 | White | 514/294 |

FOREIGN PATENT DOCUMENTS

| | | |
|---|---|---|
| 2146707 | 10/1995 | Canada . |
| 0 623 592 | 4/1994 | European Pat. Off. . |
| 0 676 395 A2 | 4/1995 | European Pat. Off. . |
| WO 95/17095 | 12/1994 | WIPO . |

OTHER PUBLICATIONS

L. S. Abovyan et al., Khim.–Farm. Zh. (1983), 17 (6):685–688.

S. Toyoshima et al., Studies of Chemotherapeutical Drugs V. Preparation of 5–Methylsulfonylfuran Derivatives and Their Antimicrobial Activities, Yakugaku Zasshi (1969), 89 (6): 779–782.

D. R. Shridhar et al., Synthesis & Biological Activity of 5–Arylsulphonyl–2–furancarboxamidine Derivatives, Indian Journal of Chemistry, vol. 19B, May 1980, pp. 386–388.

R. J. Cremlyn et al., Some Hetrocyclic Sulfonyl Chlorides and Derivatives, J. Heterocyclic Chem. (1981), 18(5): 997–1006.

D. R. Shridhar et al., Synthesis & Biological Activity of Some 5–Substituted N–(2–Amidinoethyl)–furan–2–carboxamiddes, Indian Journal of Chemistry, vol. 23B, Jun. 1984, pp. 586–588.

R. Kada et al., Reaction of Ethyl 5–Substituted–2–Furoylmalonates with Secondary Amines, Coll. Czech. Chem. Commun. (1994), 59 (6): pp. 1400–1407.

R. Bossio et al., Studies of Isocyanides and Related Compounds. Synthesis of a Novel Class of Furan Derivatives, Liebigs Ann. Chem. (1994), 5: pp. 527–528.

*Primary Examiner*—Bernard Dentz
*Attorney, Agent, or Firm*—Burns, Doane, Swecker & Mathis, L.L.P.; William H. Benz, Esq.

[57] ABSTRACT

Disclosed are furansulfonic acid derivatives and pharmaceutical compositions containing such derivatives. The disclosed compositions are useful for preventing and/or treating neurodegenerative, autoimmune and inflammatory conditions in mammals.

65 Claims, 2 Drawing Sheets

FURANSULFONIC ACID DERIVATIVES AND PHARMACEUTICAL COMPOSITIONS CONTAINING THE SAME

CROSS-REFERENCE TO RELATED APPLICATIONS

This application claims the benefit of U.S. Provisional Application No. 60/055,916, filed Aug. 18, 1997, which application is incorporated herein by reference in its entirety.

BACKGROUND OF THE INVENTION

1. Field of the Invention

This invention relates to novel furansulfonic acid derivatives and to pharmaceutical compositions containing such derivatives. This invention also relates to methods for preventing and/or treating neurodegenerative, autoimmune and inflammatory conditions in mammals using furansulfonic acid derivatives.

2. State of the Art

Alzheimer's disease is a neurodegenerative condition in which nerve cells in the brain are systematically destroyed resulting in progressive memory loss, mental confusion and ultimately death. The National Institute on Aging (NIA) has recently estimated that about 4 million people in the United States are currently afflicted with Alzheimer's disease. At present, there is no treatment that effectively prevents the disease or reverses the progressive degeneration.

In recent years, significant progress has been made in understanding the pathogenesis of Alzheimer's disease. For example, it is now known that patients with Alzheimer's disease develop amyloid plaque deposits around and between the nerve cells of their brain. These plaque deposits are made up of fibrillar aggregates of a small peptide called amyloid β-peptide or Aβ. The plaque deposits initially form in the hippocampus and cortex regions of the brain (areas associated with memory and cognition) and then spread to other areas as the disease progresses. The deposition of fibrils and plaques is also followed by inflammation of the surrounding support cells, called glia, which may lead to further loss of neurons. Eventually, the nerve cells in the brains of most Alzheimer's patients develop tangles of a microtubule-associated protein, called tau, which are believed to be a response by the nerve cells to damage.

Progress in understanding the underlying mechanisms of Alzheimer's disease has led to the development of various in vitro and in vivo models to identify compounds effective for preventing and/or treating Alzheimer's disease and other neurodegenerative conditions. In one such in vitro model, compounds are evaluated for their ability to intervene in Aβ(1-40) or Aβ(1-42) beta-pleated sheet formation. Since the deposition of amyloid β-peptide is associated with the development of Alzheimer's disease, compounds which effectively disrupt the formation of Aβ(1-40) or Aβ(1-42) beta-pleated sheets are potentially useful for preventing and/or reversing Alzheimer's disease-related amyloid deposits.

In another in vitro model, compounds are evaluated for their ability to protect against Aβ(25-35)-induced neuronal cell loss in rat embryonic hippocampal neuronal/astrocytes cultures. As discussed above, patients with Alzheimer's disease suffer a progressive loss of neuronal cells. Accordingly, compounds which are effective in this in vitro test are potentially useful for reducing or preventing neuronal cell loss in patients afflicted with Alzheimer's disease or other neurodegenerative conditions.

A third in vitro Alzheimer's disease model is based on the observation that β-amyloid increases the release of cytokines, such as interleukin-1β (IL-1β), interleukin-6 (IL-6) and tumor necrosis factor-α (TNFα), in human monocyte cells. IL-1β, IL-6 and TNFα are proteins associated with inflammatory and immune responses. As previously mentioned, the deposition of fibrils in the brains of Alzheimer's patients is associated with inflammation of the surrounding support cells. See, S. D. Yan et al., *Proc. Natl. Acad. Sci. USA*, 94, 5296 (1997). Thus, compounds effective in this in vitro test are potentially useful for reducing and/or preventing the inflammation associated with Alzheimer's disease.

Additionally, elevated levels of IL-1β, IL-6, TNFα and other cytokines are associated with a wide variety of inflammatory and autoimmune conditions, including septic shock, rheumatoid arthritis, erythema nodosum leprosy, meningococcal meningitis, multiple sclerosis, systemic lupus and the like. See, L. Sekut et al., *Drug News Perspect.* 1196, 9, 261; and A. Waage et al., *J. Exp. Med.* 1989, 170, 1859–1867. Accordingly, compounds which inhibit the production of such cytokines are potentially useful for treating such inflammatory and autoimmune conditions.

Similarly, various in vivo disease models are available for identifying compounds useful for preventing and/or treating neurodegenerative, autoimmune and inflammatory conditions. One such in vivo disease model is based on the observation that mammals suffer locomotor impairment when Aβ(25-35) is injected into the substantia nigra region of their brain. Since amyloid β-peptide deposits are associated with Alzheimer's disease, compounds which effectively reduce the locomotor impairment of mammals injected with Aβ(25-35) are potentially useful for the prevention and/or treatment of Alzheimer's disease and other neurodegenerative conditions. Another in vivo disease model is based on the observation that certain strains of autoimmune mice develop cognitive deficits as they mature. See, for example, Forster et al., *Behav. Neural Biology* 1988, 49, 139–151. Thus, compounds which prevent or reduce such cognitive deficits are potentially useful for preventing and/or treating neurodegenerative and autoimmune conditions.

It has now been discovered that certain novel furansulfonic acid derivatives effectively inhibit the formation of Aβ(1-40) beta-pleated sheets and/or protect against neuronal cell loss and/or inhibit the release of cytokines, such as IL-1β, IL-6 and TNFα. Additionally, in in vivo tests, such compounds have been found to reduce the locomotor impairment caused by Aβ(25-35) and to reduce the cognitive deficits that develop in certain strains of autoimmune mice.

SUMMARY OF THE INVENTION

This invention provides novel furansulfonic acid derivatives which are useful for preventing and/or treating neurodegenerative, autoimmune and inflammatory conditions in mammals. In particular, the compounds of this invention are useful for preventing and/or treating Alzheimer's disease.

Accordingly, in one of its composition aspects, this invention is directed to compounds of formula I:

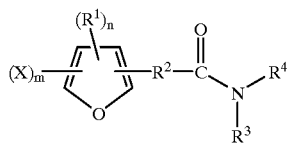

I wherein
each $R^1$ is independently selected from the group consisting of hydrogen, alkyl, alkenyl, alkynyl, alkaryl, aryl, alkoxy, alkcycloalkyl, cycloalkyl, cycloalkenyl and halo;

$R^2$ is selected from the group consisting of alkylene, alkenylene and a covalent bond;

$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

m is an integer from 1 to 3; and n is an integer from 0 to 2, provided that m+n=3.

Preferably, in the compounds of formula I above, $R^1$ is selected from the group consisting of hydrogen and alkyl. More preferably, $R^1$ is hydrogen.

$R^2$ is preferably selected from the group consisting of an alkylene group of the formula —$(CH_2)_p$—, wherein p is an integer from 1 to 6; an alkenylene group of the formula —$CR^7$=$CR^8$—, wherein $R^7$ and $R^8$ are independently selected from the group consisting of hydrogen and lower alkyl; and a covalent bond. More preferably, $R^2$ is selected from the group consisting of —$CH_2CH_2$—, —CH=CH— and a covalent bond.

Preferably, $R^3$ and $R^4$ are independently selected from the group consisting of hydrogen, alkyl and cycloalkyl, provided that $R^3$ and $R^4$ are not both hydrogen. Alternatively, $R^3$ and $R^4$ are preferably joined together to form a cycloalkyl group having 4 or 6 carbon atoms. More preferably, $R^3$ is hydrogen and $R^4$ is lower alkyl or cycloalkyl. Still more preferably, $R^3$ is hydrogen and $R^4$ is isopropyl, n-butyl or cyclohexyl.

X is preferably —$SO_3Y$ or —$SO_2NR^5R^6$, where $R^5$ and $R^6$ are independently selected from the group consisting of hydrogen, alkyl and cycloalkyl. Alternatively, $R^5$ and $R^6$ are preferably joined together to form a cycloalkyl ring having 4 to 6 carbon atoms. More preferably, when X is —$SO_2NR^5R^6$, $R^5$ is hydrogen and $R^6$ is selected from the group consisting of hydrogen, alkyl and cycloalkyl.

Preferably, m in formula I above is 1 or 2. More preferably, m is 1.

In another of its composition aspects, this invention is directed to a compound of formula II or III:

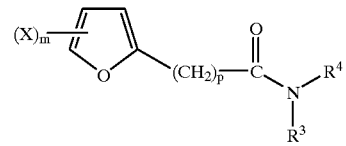

II

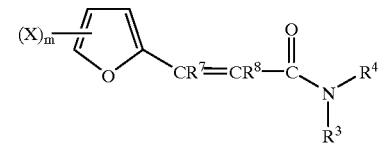

III wherein $R^3$, $R^4$, X and m are as defined above; and $R^7$ and $R^8$ are independently selected from the group consisting of hydrogen and lower alkyl; and p is an integer from 0 to 6.

Preferably, in formula III above, $R^7$ and $R^8$ are both hydrogen. In formula II above, p is preferably 0, 1 or 2. More preferably, p is 0 or 2.

In still another of its composition aspects, this invention is directed to a compound of formula IV:

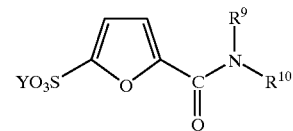

IV wherein
$R^9$ and $R^{10}$ are independently selected from the group consisting of hydrogen, lower alkyl and cycloalkyl, provided that $R^9$ and $R^{10}$ are not both hydrogen; or $R^9$ and $R^{10}$ are joined together to form a cycloalkyl ring having 4 to 6 carbon atoms; and Y selected from the group consisting of hydrogen and a pharmaceutically acceptable cation.

Preferably, in formula IV above, $R^9$ is hydrogen and $R^{10}$ is isopropyl, n-butyl or cyclohexyl. Alternatively, in another preferred embodiment, $R^9$ and $R^{10}$ are joined together to form a cycloalkyl ring having 4 to 6 carbon atoms. Preferably, in formula IV above, Y is hydrogen or a sodium cation.

In yet another of its composition aspects, this invention is directed to a compound of formula V:

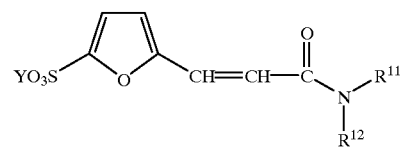

V wherein
$R^{11}$ and $R^{12}$ are independently selected from the group consisting of hydrogen, lower alkyl and cycloalkyl, provided that $R^{11}$ and $R^{12}$ are not both hydrogen; or $R^{11}$ and $R^{12}$ are joined together to form a cycloalkyl ring having 4 to 6 carbon atoms; and Y selected from the group consisting of hydrogen and a pharmaceutically acceptable cation.

Preferably, in formula V above, $R^{11}$ is hydrogen and $R^{12}$ is isopropyl, n-butyl or cyclohexyl. Alternatively, in another preferred embodiment, $R^{11}$ and $R^{12}$ are joined together to form a cycloalkyl ring having 4 to 6 carbon atoms. Preferably, in formula V above, Y is hydrogen or a sodium cation.

In still yet another of its composition aspects, this invention is directed to a compound of formula VI:

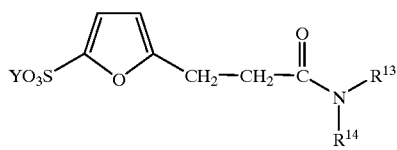

VI wherein $R^{13}$ and $R^{14}$ are independently selected from the group consisting of hydrogen, lower alkyl and cycloalkyl, provided that $R^{13}$ and $R^{14}$ are not both hydrogen; or $R^{13}$ and $R^{14}$ are joined together to form a cycloalkyl ring having 4 to 6 carbon atoms; and Y selected from the group consisting of hydrogen and a pharmaceutically acceptable cation.

Preferably, in formula VI above, $R^{13}$ is hydrogen and $R^{14}$ is isopropyl, n-butyl or cyclohexyl. Alternatively, in another preferred embodiment, $R^{13}$ and $R^{14}$ are joined together to form a cycloalkyl ring having 4 to 6 carbon atoms. Preferably, in formula VI above, Y is hydrogen or a sodium cation.

In another of its composition aspects, this invention is directed to a compound selected from the group consisting of:

N-n-butyl-5-carbamoylfuran-2-sulfonic acid
N-isopropyl-5-carbamoylfuran-2-sulfonic acid
N-cyclohexyl-5-carbamoylfuran-2-sulfonic acid
5-(1-piperidylcarbonyl)furan-2-sulfonic acid
5-[2-(N-n-butylcarbamoyl)eth-1-enyl]furan-2-sulfonic acid
5-[2-(N-n-butylcarbamoyl)ethyl]furan-2-sulfonic acid
N-n-butyl-5-(N-n-butylcarbamoyl)furan-2-sulfonamide
N,N-diethyl-5-(N,N-diethylcarbamoyl)furan-2-sulfonamide, and pharmaceutically acceptable salts thereof.

Particularly preferred compounds include those shown in Tables I, II and III and pharmaceutically acceptable salts thereof (i.e., the sodium salts).

TABLE I

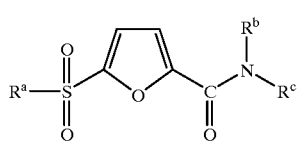

| Example No. | $R^a$ | $R^b$ | $R^c$ |
|---|---|---|---|
| 1 | HO— | H— | $CH_3CH_2CH_2CH_2$— |
| 2 | HO— | H— | $(CH_3)_2CH$— |
| 3 | HO— | H— | cyclohexyl- |
| 4 | HO— | $R^b/R^c =$ | $—CH_2CH_2CH_2CH_2CH_2$— |
| 7 | $CH_3CH_2CH_2CH_2NH$— | H— | $CH_3CH_2CH_2CH_2$— |
| 8 | $(CH_3CH_2)_2N$— | $CH_3CH_2$— | $CH_3CH_2$— |

TABLE II

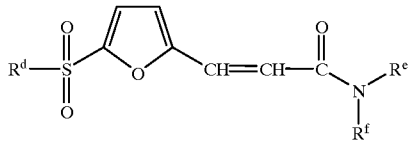

| Example No. | $R^d$ | $R^e$ | $R^f$ |
|---|---|---|---|
| 5 | HO— | H— | $CH_3CH_2CH_2CH_2$— |

TABLE III

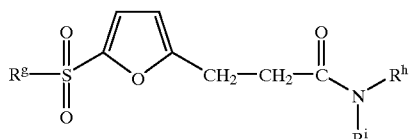

| Example No. | $R^g$ | $R^h$ | $R^i$ |
|---|---|---|---|
| 6 | HO— | H— | $CH_3CH_2CH_2CH_2$— |

This invention is also directed to pharmaceutical compositions comprising a pharmaceutically acceptable carrier and a pharmaceutically effective amount of a compound of formula I:

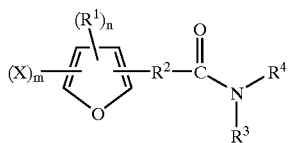

I wherein $R^1$–$R^4$, n and m are as defined above.

In additional composition aspects, this invention is directed to pharmaceutical compositions comprising a pharmaceutically acceptable carrier and a pharmaceutically effective amount of a compound of formula II, III, IV, V or VI, which formulae are defined above.

As previously mentioned, the furansulfonic acid derivatives of this invention have been discovered to inhibit the formation of Aβ(1-40) beta-pleated sheets and/or to protect against Aβ(25-35)-induced neuronal cell loss and/or to reduce β-amyloid-induced release of cytokines, such as IL-1β, IL-6 and TNFα, in human monocyte cells. Such compounds have also been found to reduce the locomotor impairment which results when Aβ(25-35) is injected into the substantia nigra of rats, and the cognitive deficits that develop in certain strains of autoimmune mice. Compounds which have such properties are useful for preventing and/or treating neurodegenerative, autoimmune and inflammatory conditions, such as Alzheimer's disease, multiple sclerosis, lupus, rheumatoid arthritis, inflammatory bowel disease, adult respiratory distress syndrome (ARDS) and the like.

Accordingly, in one of its method aspects, this invention is directed to a method for treating a patient with a neurodegenerative disease which method comprises administering to said patient a pharmaceutical composition comprising a pharmaceutically acceptable carrier and an effective neurodegenerative disease-treating amount of a compound of formula I:

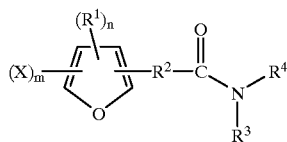

wherein $R^1$–$R^4$, n and m are as defined above.

In other method aspects, this invention is directed to methods for treating a patient with a neurodegenerative disease which methods comprise administering to said patient a pharmaceutical composition comprising a pharmaceutically acceptable carrier and an effective neurodegenerative disease-treating amount of a compound of formula II, III, IV, V or VI, which formulae are defined above.

In yet another of its method aspects, this invention is directed to a method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a compound of formula I:

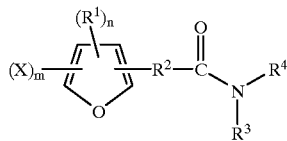

wherein $R^1$–$R^4$, n and m are as defined above.

In still other method aspects, this invention is directed to methods for preventing the onset of a neurodegenerative disease in a patient at risk for developing the neurodegenerative disease which methods comprise administering to said patient a pharmaceutical composition comprising a pharmaceutically acceptable carrier and an effective neurodegenerative disease-preventing amount of a compound of formula II, III, IV, V or VI, which formulae are defined above.

In another of its method aspects, this invention is directed to methods for treating a patient with an autoimmune disease which methods comprise administering to said patient a pharmaceutical composition comprising a pharmaceutically acceptable carrier and an effective autoimmune disease-treating amount of a compound of formula I, II, III, IV, V or VI, which formulae are defined above.

In yet another of its method aspects, this invention is directed to a method for preventing the onset of an autoimmune disease in a patient at risk for developing the autoimmune disease which method comprises administering to said patient a pharmaceutical composition comprising a pharmaceutically acceptable carrier and an effective autoimmune disease-preventing amount of a compound of formula I, II, III, IV, V or VI, which formulae are defined above.

In still another of its method aspects, this invention is directed to methods for treating a patient with an inflammatory disease which methods comprise administering to said patient a pharmaceutical composition comprising a pharmaceutically acceptable carrier and an effective inflammatory disease-treating amount of a compound of formula I, II, III, IV, V or VI, which formulae are defined above.

In yet another of its method aspects, this invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a compound of formula I, II, III, IV, V or VI, which formulae are defined above.

In another of its aspects, this invention is directed to the use of a compound of formula I, II, III, IV, v or VI in the manufacture of a formulation or medicament for a medicinal treatment. Preferably, the medical treatment is the therapeutic or prophylactic treatment of a neurodegenerative disease, an autoimmune disease or an inflammatory disease.

And, in still another of its method aspects, this invention is directed to a process for preparing a carbamoyl-substituted furansulfonic acid of formula I':

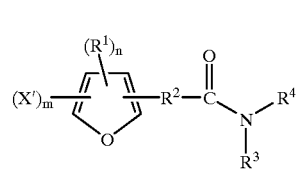

wherein each $R^1$ is independently selected from the group consisting of hydrogen, alkyl, alkenyl, alkynyl, alkaryl, aryl, alkoxy, alkcycloalkyl, cycloalkyl, cycloalkenyl and halo;

$R^2$ is selected from the group consisting of alkylene, alkenylene and a covalent bond;

$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

each X' is —$SO_3Y$, wherein Y is hydrogen or a pharmaceutically acceptable cation;

m is an integer from 1 to 3; and n is an integer from 0 to 2, provided that m+n=3; said process comprising the steps of:

(a) reacting a furan carboxylic acid halide of the formula:

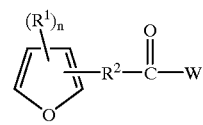

wherein $R^1$, $R^2$ and n are as defined above and W is chloro or bromo, with an amine of the formula:

wherein $R^3$ and $R^4$ are as defined above, to provide a furan carboxamide of the formula:

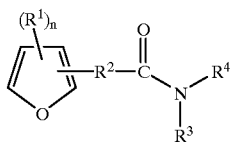

and (b) reacting the furan carboxamide with a sulfonating reagent to provide the carbamoyl-substituted furan sulfonic acid.

Preferably, the sulfonating reagent employed in this process is sulfur trioxide pyridine complex.

DETAILED DESCRIPTION OF THE INVENTION

Figure 1:
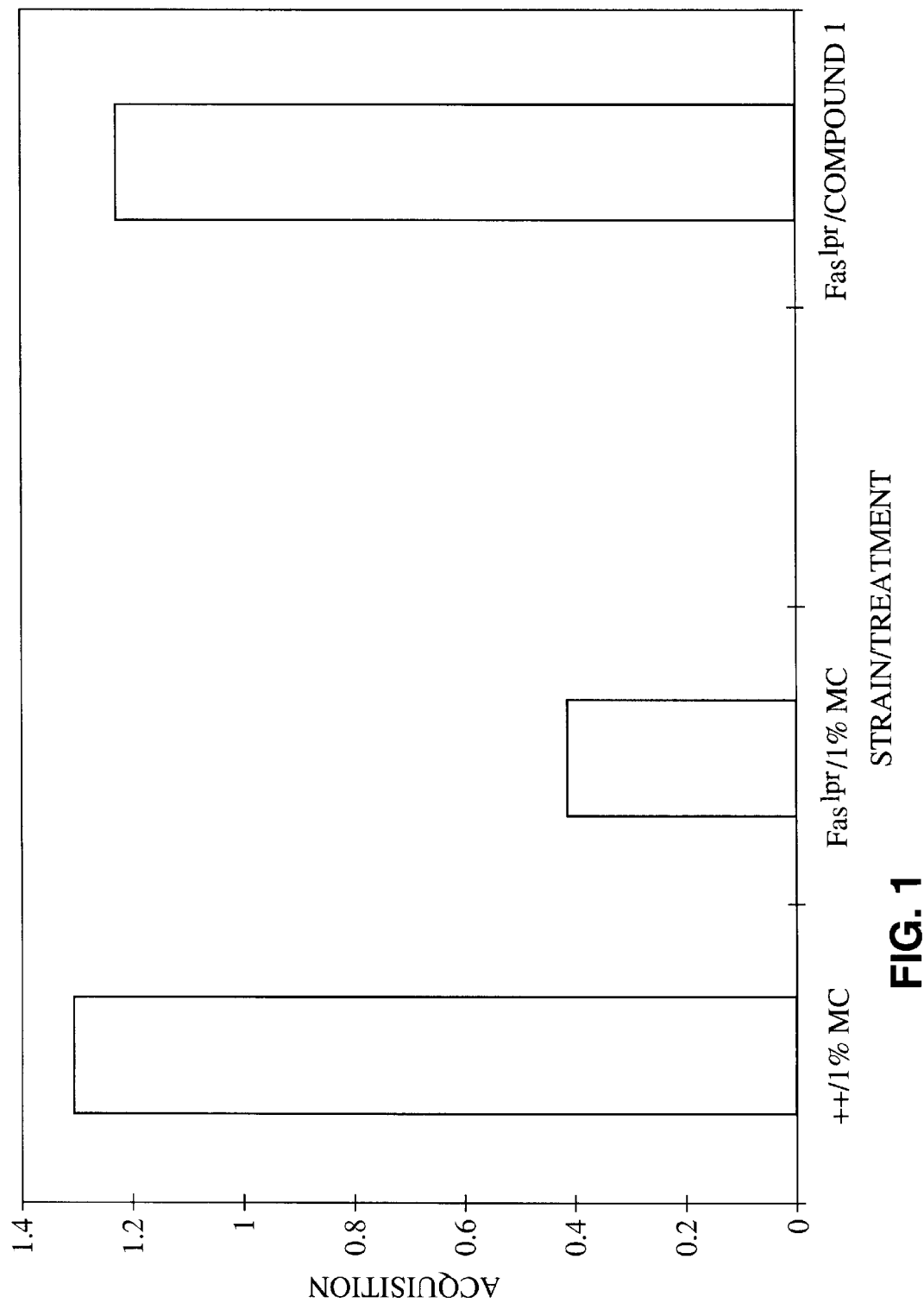
FIG. 1 is a bar graph illustrating the acquisition scores for MRL wild-type mice ("++") treated with 1% methylcellulose ("MC"), and $Fas^{lpr}$ mutant strains of mice treated with 1% methylcellulose or 100 mg/kg of N-n-butyl-5-carbamoylfuran-2-sulfonic acid sodium salt ("Compound 1").

As discussed above, the furansulfonic acid derivatives of this invention are useful for preventing and/or treating neurodegenerative, autoimmune and inflammatory conditions in mammals. When describing such compounds or pharmaceutical compositions containing such compounds or methods of using such compounds, the following terms have the following meanings unless otherwise indicated.

Definitions

The term "β-amyloid peptide" refers to a 39-43 amino acid peptide having a molecular weight of about 4.2 kD, which peptide is substantially homologous to the form of the peptide described by Glenner, et al., *Biochem. Biophys. Res. Commun.*, 120:885–890 (1984), including mutations and post-translational modifications of the normal β-amyloid peptide.

The term "cytokines" refers to peptide or protein mediators that are produced by immune cells to modulate cellular functions. Examples of cytokines include, interleukin-1β (IL-1β), interleukin-6 (IL-6) and tumor necrosis factor-α (TNFα).

"Alkyl" refers to monovalent alkyl groups preferably having from 1 to about 12 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 6 carbon atoms.

"Alkylene" refers to divalent alkylene groups preferably having from 1 to 10 carbon atoms and more preferably 1 to 6 carbon atoms which can be straight chain or branched. This term is exemplified by groups such as methylene (—CH₂—), ethylene (—CH₂CH₂—), the propylene isomers (e.g., —CH₂CH₂CH₂— and —CH(CH₃)CH₂—) and the like.

"Alkenylene" refers to divalent alkenylene groups preferably having from 2 to 10 carbon atoms and more preferably 2 to 6 carbon atoms which can be straight chain or branched and having at least 1 and preferably from 1–2 sites of alkenyl unsaturation. This term is exemplified by groups such as ethenylene (—CH=CH—), the propenylene isomers (e.g., —CH=CHCH₂— and —C(CH₃)=CH— and —CH=C(CH₃)—) and the like.

"Alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl, and the like.

"Alkcycloalkyl" refers to -alkylene-cycloalkyl groups preferably having from 1 to 10 carbon atoms in the alkylene moiety and from 3 to 8 carbon atoms in the cycloalkyl moiety. Such alkcycloalkyl groups are exemplified by —CH₂-cyclopropyl, —CH₂-cyclopentyl, —CH₂CH₂-cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to the group —C(O)OR where R is alkyl.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH₂), n-propenyl (—CH₂CH=CH₂), isopropenyl (—C(CH₃)=CH₂), and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH₂C≡CH), and the like.

"Aminocarbonyl" refers to the group —C(O)NRR where each R is independently hydrogen or alkyl.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 3 substituents selected from the group consisting of alkyl, alkoxy, alkenyl, alkynyl, amino, aminoacyl, aminocarbonyl, alkoxycarbonyl, aryl, carboxyl, cyano, halo, hydroxy, nitro, trihalomethyl and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Heterocycle" or "heterocyclic" refers to a monovalent saturated or unsaturated group having a single ring or multiple condensed rings, from 1 to 10 carbon atoms and from 1 to 4 hetero atoms selected from nitrogen, sulfur or oxygen within the ring. Examples of heterocycles include, but are not limited to, morpholine, piperazine, imidazolidine and the like.

"Pharmaceutically acceptable salt" refers to pharmaceutically acceptable salts which are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically acceptable cation" refers to a pharmaceutically acceptable cationic counterion of an acidic functional group. Such cations are exemplified by sodium, potassium, calcium, magnesium, ammonium, tetraalkylammonium cations, and the like.

General Synthetic Procedures

The furansulfonic acid derivatives of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis,* Second Edition, Wiley, New York, 1991, and references cited therein.

In a preferred method of synthesis, the furansulfonic acid derivatives of this invention are prepared by first coupling a furan carboxylic acid of formula VII:

VII

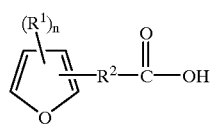

wherein $R^1$, $R^2$ and n are as defined above, with an amine of formula VIII:

VIII

VIII

wherein $R^3$ and $R^4$ are as defined above, to provide a furan carboxamide of formula IX:

IX

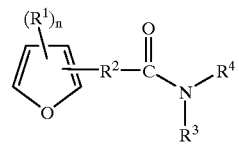

wherein $R^1$–$R^4$ and n are as defined above.

The furan carboxylic acids of formula VII are either known compounds or can be prepared from known compounds by conventional procedures. Preferred furan carboxylic acid starting materials include 2-furoic acid (furan-2-carboxylic acid), 3-furoic acid, 3-(furan-2-yl)propionic acid, 3-(furan-3-yl)propionic acid, 3-(furan-2-yl)prop-2-enoic acid, 3-(furan-3-yl)prop-2-enoic acid and the like.

The amines of formula VIII are also known compounds or compounds that can be prepared from known compounds by conventional procedures. Preferred amines for use in this invention include methylamine, ethylamine, n-propylamine, isopropylamine, n-butylamine, isobutylamine, sec-butylamine, tert-butylamine, n-pentylamine, cyclopentylamine, n-hexylamine, cyclohexylamine, n-octylamine, tert-octylamine, dimethylamine, diethylamine, di-n-propylamine, -diisopropylamine, di-n-butylamine, diisobutylamine, di-sec-butylamine, di-n-hexylamine, methylethylamine, methyl-n-propylamine, methylisopropylamine, -methyl-n-butylamine, methyl-tert-butylamine, methyl-tert-octylamine, methylcyclopentylamine, methylcyclohexylamine, ethyl-n-propylamine, ethylisopropylamine, ethyl-n-butylamine, ethylcyclohexylamine, phenylamine, (4-methyl) phenylamine, pyrrolidine, piperidine, morpholine and the like. Especially preferred amines include, isopropylamine, n-butylamine, cyclohexylamine, diethylamine and piperidine.

The coupling reaction of furan carboxylic acid VII with amine VIII can be conducted using any conventional coupling reagent including, for example, carbodiimides such as dicyclohexylcarbodiimide and other promoting agents, such as N,N'-carbonyldiimidazole. This reaction can be conducted with or without the use of well known additives such as N-hydroxysuccinimide, 1-hydroxybenzotriazole, etc. which are known to facilitate the coupling of carboxylic acids and amines.

Alternatively, in a preferred embodiment, the acid halide of compound VII can be employed in the coupling reaction. The acid halide of VII can be prepared by contacting VII with an inorganic acid halide, such as thionyl chloride, phosphorous trichloride, phosphorous tribromide or phosphorous pentachloride, or alternatively, with oxalyl chloride under conventional conditions. Generally, this reaction is conducted using about 1 to 5 molar equivalents of the inorganic acid halide or oxalyl chloride, either neat or in an inert solvent, such as carbon tetrachloride, at temperature in the range of about 0° C. to about 80° C. for about 1 to about 48 hours. A catalyst, such as N,N-dimethylformamide, may also be used in this reaction.

When an acyl halide is employed in the coupling reaction, it is typically reacted with amine VIII in the presence of a suitable base to scavenge the acid generated during the reaction. Suitable bases include, by way of example, triethylamine, diisopropylethylamine, N-methylmorpholine and the like. Alternatively, an excess of amine VIII may be used to scavenge the acid generated during the reaction.

The coupling reaction using either furan carboxylic acid VII or its acid halide is preferably conducted at a temperature of from about 0° C. to about 60° C. for about 1 to about 24 hours. Typically, the reaction is conducted in an inert aprotic polar solvent such as dimethylformamide, dichloromethane, chloroform, acetonitrile, tetrahydrofuran and the like using about 1 to about 5 molar equivalents of the amine based on the furan carboxylic acid or its acid halide. Upon completion of the reaction, the furan carboxamide IX is recovered by conventional methods including precipitation, chromatography, filtration, distillation and the like.

The furan carboxamide IX is then sulfonated used conventional sulfonating reagents to provide furansulfonic acid derivatives of formula I above, wherein X is —SO$_3$Y and Y is as defined above. A preferred sulfonating reagent for use in this reaction is sulfur trioxide pyridine complex. Typically, the sulfonation reaction is conducted by contacting the furan carboxamide IX with about 1 to about 5 molar equivalent of the sulfonating reagent in an inert solvent, such as 1,2-dichloroethane, at a temperature ranging from about 50° C. to about 200° C., preferably at about 100° C. to about 150° C., for about 6 to about 48 hours. Upon completion of the reaction, the furansulfonic acid compound is recovered by conventional methods including precipitation, chromatography, filtration and the like. Surprisingly, the yield for this sulfonation reaction is significantly higher than that obtained for sulfonation of the corresponding furan carboxylic acid VII under similar conditions.

The furan sulfonamide derivatives of formula I, i.e., those compounds wherein X is —SO$_2$NR$^5$R$^6$ where R$^5$ and R$^6$ are as defined above, are readily prepared from the corresponding chlorocarbonylfuran sulfonyl chloride of formula X:

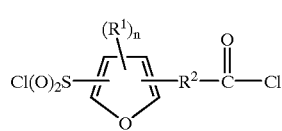

wherein R$^1$, R$^2$ and n are as defined above, by reaction with an amine of formula XI:

wherein R$^5$ and R$^6$ are as defined above, under conventional reaction conditions.

The amines of formula XI are either known compounds or compounds that can be prepared by known procedures. Examples of suitable amines for use in this reaction include, but are not limited to, methylamine, ethylamine, n-propylamine, isopropylamine, n-butylamine, isobutylamine, sec-butylamine, tert-butylamine, n-pentylamine, cyclopentylamine, n-hexylamine, cyclohexylamine, n-octylamine, tert-octylamine, dimethylamine, diethylamine, di-n-propylamine, -diisopropylamine, di-n-butylamine, diisobutylamine, di-sec-butylamine, di-n-hexylamine, methylethylamine, methyl-n-propylamine, methylisopropylamine, -methyl-n-butylamine, methyl-tert-butylamine, methyl-tert-octylamine, methyl-cyclopentylamine, methylcyclohexylamine, ethyl-n-propylamine, ethylisopropylamine, ethyl-n-butylamine, ethylcyclohexylamine, phenylamine, (4-methyl) phenylamine, pyrrolidine, piperidine, morpholine and the like.

The chlorocarbonylfuran sulfonyl chlorides of formula X are also known compounds or compounds which can be prepared from known compounds by conventional procedures. Typically, these compounds are prepared from the corresponding carboxyfuran sulfonic acid by treatment with phosphorous oxychloride and phosphorous pentachloride. This reaction is generally conducted by contacting the carboxyfuran sulfonic acid with about 2 to about 10 equivalents of phosphorous oxychloride and about 2 to about 5 equivalents of phosphorous pentachloride at a temperature ranging from about 0° C. to about 30° for about 1 to 12 hours. The carboxyfuran sulfonic acids employed in this reaction are either known compounds or compounds which can be prepared from known compounds by conventional procedures. For example, carboxyfuran sulfonic acids can be prepared from the corresponding formylfuran sulfonic acids by oxidation using conventional oxidizing agents, such as potassium dichromate.

The sulfonamide derivatives of formula I in which R$^5$=R$^3$ and R$^6$ =R$^4$, i.e., those compounds in which the carboxamide and sulfonamide groups are derived from the same amine, are readily prepared by contacting the sulfonyl chloride X with an excess of amine XI, preferably with about 2 to about 5 equivalents of amine XI. Typically, this reaction is conducted in the presence of a suitable base to scavenge the acid generated during the reaction. Suitable bases include, by way of example, triethylamine, diisopropylethylamine, N-methylmorpholine and the like. Alternatively, an excess of amine XI may be used to scavenge the acid generated during the reaction.

Reaction of the sulfonyl chloride X with amine XI is preferably conducted at a temperature ranging from about 0° C. to about 60° C. for about 1 to about 24 hours. Upon completion of the reaction, the resulting carbamoylfuran sulfonamide is recovered by conventional methods including precipitation, chromatography, filtration, and the like.

The sulfonamide derivatives of formula I in which R$^5$ R$^3$ and/or R$^6$ R$^4$, i.e., those compounds in which the carboxamide and sulfonamide groups are derived from different amines, can be prepared by first selectively reacting the chlorocarbonylfuran sulfonyl chloride with an alcohol, such as methanol or ethanol, under conventional conditions to form the corresponding alkoxycarbonylfuran sulfonyl chloride. See, for example, L. S. Abovyan et al., *Khim.-Farm. Zh.* (1983),17(6) 685–688. The alkoxycarbonylfuran sulfonyl chloride is then reacted with about 1 to about 5 equivalents of amine XI to afford the corresponding alkoxycarbonylfuran sulfonamide. This reaction is preferably conducted at a temperature ranging from about 0° C. to about 60° C. for about 1 to about 24 hours in the presence of a suitable base, such as triethylamine, to scavenge the acid generated during the reaction. Alternatively, an excess of amine XI may be used to scavenge the acid generated during the reaction.

The ester group of the alkoxycarbonylfuran sulfonamide is then hydrolyzed under conventional conditions to form the corresponding carboxyfuran sulfonamide. This reaction is typically conducted by contacting the alkoxycarbonylfuran sulfonamide with about 1 to about 1.2 equivalents of an alkali metal hydroxide, such as lithium hydroxide, sodium hydroxide or potassium hydroxide, in a suitable solvent, such as tetrahydrofuran/water or dioxane/water, at a temperature ranging from about 0° C. to about 25° C. for about 1 to 24 hours. The resulting carboxyfuran sulfonamide can then be coupled to amine IV using the procedures described above to provide the corresponding carbamoylfuran sulfonamide of formula I.

Alternatively, in another preferred method of synthesis, the furansulfonic acid derivatives of this invention having formula XII:

XII

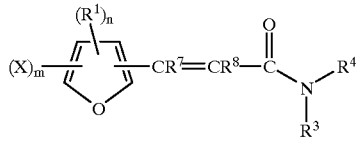

wherein $R^1$, $R^3$, $R^4$, $R^7$, $R^8$, X, m and n are as defined above, can be prepared by reacting a furan carbonyl compound of formula XIII:

XIII

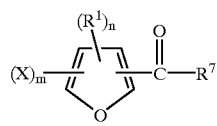

wherein $R^1$, $R^7$, X, m and n are as defined above, with a Wittig reagent of formula XIV:

XIV

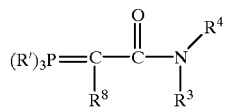

wherein $R^3$, $R^4$ and $R^8$ are as defined above, and each R' is preferably aryl, such as phenyl, or two of R' are preferably alkyl, such as methyl, ethyl and the like, and the remaining R' is =O.

The furan carbonyl compounds of formula XIII are either known compounds or compounds that can be prepared from known compounds by conventional procedures. Preferred furan carbonyl compounds for use in this invention include, but are not limited to, 5-formylfuran-2-sulfonic acid, 4-formylfuran-2-sulfonic acid, 3-formylfuran-2-sulfonic acid, 5-acetylfuran-2-sulfonic acid and the like.

The Wittig reagents of formula XIV are also known compounds or compounds that can be prepared from known compounds by conventional procedures. Typically, the Wittig reagent is prepared by first contacting a triaryl phosphine, such as triphenylphosphine, or a trialkyl phosphite, such as trimethyl phosphite or triethyl phosphite, with an α-halo carboxamide of formula XV:

XV

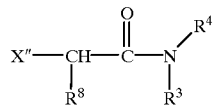

wherein $R^3$, $R^4$ and $R^8$ are as defined above, and X" is chloro, bromo or iodo, to form a triarylphosphonium salt or a phosphonate ester. This reaction is typically conducted in an inert solvent, such as toluene and the like, at a temperature ranging from about 50° C. to about 150° C. for about 24 to about 48 hours. The Wittig reagent XIV is then formed by treatment of the triarylphosphonium salt or the phosphonate ester with at least one molar equivalent of a strong base, such as n-butyl lithium and the like. Preferably, the Wittig reagent XIV is generated in situ just prior to reaction with the furan carbonyl compound XIII.

The Wittig reaction is typically conducted by contacting the furan carbonyl compound XIII with about 1 to about 2 molar equivalents of the Wittig reagent XIV. When the X group in formula XIII above is —$SO_3H$, the sulfonate group is generally converted to a suitable salt, such as the sodium or lithium salt, by treatment with a base, such as sodium hydride, prior to reaction with the Wittig reagent. The Wittig reaction is typically conducted at a temperature ranging from about –20° C. to about 80° C., preferably about 0° to about 5° C., for about 1 to about 24 hours in an inert solvent, such as tetrahydrofuran. Upon completion of the reaction, the furansulfonic acid of formula XIII is recovered by conventional methods including precipitation, chromatography, filtration, and the like.

Additionally, in a further preferred method of synthesis, the furansulfonic acid derivatives of formula XII above can be hydrogenated using conventional reagents and conditions to provide for compounds in which the unsaturation between the furan ring and the amide group has been saturated. This reaction is typically conducted by hydrogenating a compound of formula XII under about 1 to about 4 atmospheres of hydrogen in the presence of catalyst, such as palladium on carbon. Generally, this reaction is conducted in an inert solvent, such as ethanol, at a temperature ranging from about 10° C. to about 60° C. for about 1 to about 48 hours. Upon completion of the reaction, the product is recovered by conventional methods including extraction, precipitation, chromatography, filtration, and the like.

Pharmaceutical Compositions

When employed as pharmaceuticals, the furansulfonic acid derivatives of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the furansulfonic acid compound in such compositions is typically a minor component, often being from about 0.05 to 10% by weight with the remainder being the injectable carrier and the like.

The above described components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in the incorporated materials in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active furansulfonic acid compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active furansulfonic acid compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active furansulfonic acid compound) in a tablet press.

Formulation 5—Injection

The compound of formula I is dissolved in a buffered sterile saline injectable aqueous medium to a concentration of approximately 5 mg/ml.

Compound Utility

The furansulfonic acid derivatives of this invention have been discovered to inhibit the formation of Aβ(1-40) beta-pleated sheets and/or protect against neuronal cell loss and/or inhibit the release of cytokines, such as IL-1β, IL-6 and TNFα. Additionally, such compounds have been found to reduce the locomotor impairment caused by Aβ(25-35) and to reduce the cognitive deficits in certain autoimmune strains of mice. As previously discussed, the formation of Aβ(1-40) beta-pleated sheets, neuronal cell loss and cognitive deficits are associated with neurodegenerative conditions, such as Alzheimer's disease, and/or autoimmune conditions. Additionally, elevated levels of cytokines are associated with neurodegenerative, autoimmune and/or inflammatory conditions. Accordingly, the compounds and pharmaceutical compositions of this invention find use as therapeutics for preventing and/or treating neurodegenerative, autoimmune and inflammatory conditions in mammals including humans.

Among the conditions which may be treated and/or prevented with the furansulfonic acid derivatives of formula I are neurodegenerative conditions, such as Alzheimer's disease, Parkinson's disease, HIV-dementia and the like; autoimmune conditions, such as systemic lupus (erythematosus) and the like; and inflammatory conditions, such as inflammatory bowel disease, rheumatoid arthritis, septic shock, erythema nodosum leprosy, septicemia, uveitis, adult respiratory distress syndrome (ARDS), multiple sclerosis and the like.

Additionally, the furansulfonic acid derivatives of this invention have been discovered to effectively inhibit the release of cytokines, such a IL-1β, IL-6 and TNFα. Elevated levels of certain cytokines are associated with a wide variety of inflammatory neurodegenerative and autoimmune conditions, including Alzheimer's disease, AIDS dementia, septic shock, rheumatoid arthritis, erythema nodosum leprosy, meningococcal meningitis, multiple sclerosis, systemic lupus and the like. See, L. Sekut et al., *Drug News Perspect.* 1996, 9, 261; K. Shiosaki et al., "Chapter 4. Emerging Opportunities in Neuroinflammatory Mechanisms of Neurodegeneration" *Annual Reports in Medicinal Chemistry*, pp. 31–40, Academic Press (1995) and reference cited therein; and A. Waage et al., *J. Exp. Med.* 1989, 170, 1859–1867. Accordingly, the furansulfonic acid derivatives of formula I are useful for treating diseases characterized by an overproduction or an unregulated production of cytokines, particularly IL-1β, IL-6 and TNFα, including neurodegenerative, autoimmune and/or inflammatory conditions.

As discussed above, the compounds described herein are suitable for use in a variety of drug delivery systems. Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of furansulfonic acid derivative, with preferred doses each providing from about 0.1 to about 10 mg/kg and especially about 1 to about 5 mg/kg.

When used to prevent the onset of a neurodegenerative, autoimmune or inflammatory condition, the furansulfonic acid derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active furansulfonic acid derivatives.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.

bd=broad doublet
bs=broad singlet
d=doublet
dd=doublet of doublets
dec=decomposed
$dH_2O$=distilled water
DIV=days in vitro
ELISA=enzyme-linked immuno-sorbent assay
EtOAc=ethyl acetate
EtOH=ethanol
FBS=fetal bovine serum
g=grams
h=hours
Hz=hertz
IL-1β=interleukin-1β
IL-6=interleukin-6
L=liter
LPS=lipopolysaccharide
m=multiplet
min=minutes
M=molar
MeOH=methanol
mg=milligram
MHz=megahertz
mL=milliliter
mmol=millimole
m.p.=melting point
N=normal
q=quartet
quint.=quintet
s=singlet
t=triplet
THF=tetrahydrofuran
ThT=thioflavin T
tlc=thin layer chromatography TNFα=tumor necrosis factor-α
μg=microgram
μL=microliter
UV=ultraviolet In the examples below, all temperatures are in degrees Celsius (unless otherwise indicated). Examples A and B describe the synthesis of various intermediates used to prepare the furansulfonic acid derivatives of this invention; Examples 1–8 describe the synthesis of furansulfonic acid derivatives; and Examples 9–13 describe the in vitro and in vivo testing of such compounds.

Example A

Synthesis of N-n-Butylfuran-2-carboxamide

To a solution of n-butylamine (99 mL, 1.0 mol) in $CH_2Cl_2$ (300 mL) was added 2-furoyl chloride (33.0 mL, 0.335 mol) dropwise at 0–5° C. with stirring. The reaction mixture was stirred for additional 2 h at 0–5° C. and overnight at room temperature. The solution was poured into a mixture of wet-ice (200 g) and 37% HCl (50 mL). After separation, the organic layer was washed with 2×200 mL water, dried over $Na_2SO_4$ and filtered. Removal of solvent provided the title compound (49.59 g, 88.6% yield) as a white solid, m.p.=43.8° C. (Rf=0.53 on a silica gel plate using EtOAc as an eluant). This product was used without further purification.

Spectroscopic data were as follows:

IR (KBr, $cm^{-1}$): 3314 (NH), 3122 (furan CH), 2959.2 (CH), 2932.9 (CH), 2872.7 (CH), 1646.5 (C=O), 1595.2 (furan ring), 1535.0 (NH), 1307.2 (C—N). $^1$H NMR ($CDCl_3$, 270 MHz): δ=7.357 (1H, dd, $J_1$=1.7 Hz, $J_2$=0.7 Hz, furan CH), 7.027 (1H, dd, $J_1$=3.5 Hz, $J_2$=0.7 Hz, furan CH), 6.416 (1H, dd, $J_1$=3.5 Hz, $J_2$=1.7 Hz, furan CH), 6.453 (1H, broad s, NH), 3.359 (2H, m, $CH_2$), 1.522 (2H, m, $CH_2$), 1.364 (2H, m, $CH_2$), and 0.881 (3H, t, J=7.3 Hz, $CH_3$). $^{13}$C NMR ($CDCl_3$, 270 MHz): δ=158.779, 148.529, 143.937, 113.888, 112.104, 38.552, 31.398, 19.653, and 13.277.

Example B

Synthesis of (N-n-Butylcarbamoyl) methyltriphenylphosphonium Chloride

A solution of triphenyl phosphine (26.23 g, 0.1 mol) and n-butyl chloroacetamide (14.96 g, 0.1 mol) in toluene (250 mL) was refluxed with stirring for 22 h. After cooling to room temperature, the mixture was filtered and dried under high vacuum to afford 36.72 g (89.1% yield) of the title compound as white crystals. This material was used without further purification.

Spectroscopic data were as follows:

$^1$H NMR (DMSO-$d_6$, 270 MHz): δ=9.209 (1H, t, J=5.5 Hz, NH), 7.786 (15H, m, 3 $C_6H_5$), 5.141 (2H, d, $J_p$=15.3 Hz, $PCH_2$), 2.912 (2H, m, $NCH_2$), 1.127 (4H, m, $CH_2CH_2$), and 0.752 (3H, t, J=7.2 Hz, $CH_3$).

Example 1

Synthesis of N-n-Butyl-5-carbamoylfuran-2-sulfonic Acid Sodium Salt

Sulfur trioxide pyridine complex (38.07 g, 239.22 mmol) and 1,2-dichloroethane (200 mL) were mixed with N-n-butylfuran-2-carboxamide (20 g, 119.61 mmol), from Example A above, in a Parr pressure reactor. The reactor was sealed and heated to 140° C. After 22 h at 140° C., the reactor was cooled to room temperature and the mixture was concentrated on a rotary evaporator to give a dark slurry. The residue was treated with a solution of $Na_2CO_3$ (27.8 g, 262 mmol) in water (200 mL) and the resulting mixture was evaporated to dryness. The resulting solid was stirred with methylene chloride (300 mL) to remove unreacted starting material and the undissolved brown solid was refluxed with ethanol (500 mL) for 30 min and then filtered. The filtrate was concentrated on a rotary evaporator to provide 25.95 grams of a solid. The solid was then dissolved in water and the resulting aqueous solution was treated with charcoal and filtered through a short column of silica gel, eluting with water (150 mL). Removal of the water afforded the sodium salt of the title compound (21.95 grams, 68.1% yield) as slightly yellowish solid, m.p.=223.6° C. ($R_f$=0.47 on a silica gel plate using 2:1 EtOAc/EtOH).

Spectroscopic data were as follows:

IR (KBr, $cm^{-1}$): 3440.5 (broad, hydrate & NH), 2960.3 (CH), 2934.3 (CH), 2873.2 (CH), 1650.2 (C=O), 1598.0 (furan ring), 1547.0 (NH), 1307.2 (C—N), 1246 ($SO_2$), 1221.7 ($SO_2$), and 1052.7 ($SO_3$). $^1$H NMR ($D_2O$, 270 MHz): δ=7.106 (1H, d, J=3.7 Hz, furan CH), 6.923 (1H, d, J=3.7 Hz, furan CH), 3.326 (2H, t, J=6.9 Hz, $CH_2N$), 1.533 (2H, m, $CH_2$), 1.329 (2H, m, $CH_2$), and 0.869 (3H, t, J=7.3 Hz, $CH_3$). $^{13}$C NMR ($D_2O$, 270 MHz): δ=160.182, 153.562, 147.918, 115.154, 113.232, 39.010, 30.346, 19.165, and 12.698.

Example 2

Synthesis of N-Isopropyl-5-carbamoylfuran-2-sulfonic Acid Sodium Salt

The title compound was prepared from N-isopropylfuran-2-carboxamide and sulfur trioxide pyridine complex using the procedure described in Example 1 above. The title compound was isolated in 36.7% yield as a solid, m.p.=237.2° C. ($R_f$=0.47 on a silica gel plate using 3:1 EtOAc/EtOH).

Spectroscopic data were as follows:

IR (KBr, $cm^{-1}$): 3305.4 (NH), 2970.8 (CH), 1659.5 (C=O), 1597.5 (furan ring), 1544.2 (NH), 1249.9 ($SO_2$), 1203.8 ($SO_2$), and 1049.8 ($SO_3$). $^1$H NMR ($D_2O$, 270 MHz): δ=7.121 (1H, d, J=3.6 Hz, furan CH), 6.936 (1H, d, J=3.6 Hz, furan CH), 4.105 (1H, septet, J=6.6 Hz, CH), and 1.224 (6H, d, J=6.6 Hz, 2 $CH_3$). $^{13}$C NMR ($D_2O$, 270 MHz): δ=159.313, 153.577, 147.964, 115.169, 113.171, 41.999, and 21.117.

Example 3

Synthesis of N-Cyclohexyl-5-carbamoylfuran-2-sulfonic Acid Sodium Salt

The title compound was prepared from N-cyclohexylfuran-2-carboxamide and sulfur trioxide pyridine complex using the procedure described in Example 1 above. The title compound was isolated in 75.3% yield as a solid, m.p.=242.5° C. (dec) ($R_f$=0.45 on a silica gel plate using 2:1 EtOAc/EtOH).

Spectroscopic data were as follows:

IR (KBr, $cm^{-1}$): 3258.0 (NH), 2933.3 (CH), 1641.1 (C=O), 1579.3 (furan ring), 1545.6 (NH), 1240.0 ($SO_2$), 1219.0 ($SO_2$), and 1049.1 ($SO_3$). $^1$H NMR ($D_2O$, 270 MHz): δ=7.141 (1H, d, J=3.7 Hz, furan CH), 6.943 (1H, d, J=3.7 Hz), 3.747 (1H, m, CHN), 1.880 (2H, m, cyclohexyl protons), 1.728 (2H, m, cyclohexyl protons), 1.584 (1H, m, cyclohexyl proton), and 1.400–1.117 (5H, m, cyclohexyl protons). $^{13}$C NMR ($D_2O$, 270 MHz): δ=159.191, 153.745, 147.873, 115.276, 113.126, 49.245, 31.840, 24.732, and 24.443.

Example 4

Synthesis of 5-(1-Piperidylcarbonyl)furan-2-sulfonic Acid Sodium Salt

The title compound was prepared from 1-(2-furoyl)piperidine and sulfur trioxide pyridine complex using the procedure described in Example 1 above. The title compound was isolated in 54.0% yield as a solid, m.p.=286.4° C. (dec) ($R_f$=0.31 on a silica gel plate using 2:1 EtOAc/EtOH).

Spectroscopic data were as follows:

IR (KBr, $cm^{-1}$): 3453.5 (broad, hydrate & NH), 2938.9 (CH), 1620.2 (C=O), 1573.5 (furan ring), 1240 ($SO_2$), 1220.9 ($SO_2$), and 1049.8 ($SO_3$). $^1$H NMR ($D_2O$, 270 MHz): δ=6.995 (1H, d, J=3.6 Hz, furan CH), 6.942 (1H, d, J=3.6 Hz, furan CH), 3.723 (2H, m, $CH_2$), 3.625 (2H, m, $CH_2$), and 1.668 (6H, m, $CH_2CH_2CH_2$). $^{13}$C NMR ($D_2O$, 270 MHz): δ32 160.228, 153.120, 147.476, 116.252, 112.637, 48.558, 44.455, 25.968, 25.114, and 23.512.

Example 5

Synthesis of 5-[2-(N-n-Butylcarbamoyl)eth-1-enyl]-furan-2-sulfonic Acid Sodium Salt To a suspension of (N-n-butylcarbamoyl)methyltriphenylphosphonium chloride (16.63 g, 40.38 mmol), from Example B above, in tetrahydrofuran (200 mL) at 0–5° C. was added a solution of n-butyllithium in hexanes (18 mL, 2.5 M, 45 mmol). Upon addition of the n-butyllithium solution, the solution became homogeneous and the reaction mixture was stirred for 10 min at 5° C. 5-Formylfuran-2-sulfonic acid sodium salt (8.0 g, 40.38 mmol) was then added in one portion and the reaction mixture was stirred for 45 min at 0–5° C. and then at room temperature for 1.75 h. The mixture was filtered and the solid obtained was stirred with THF (100 mL) for several hours and then filtered. The solid was mixed with ethanol (200 mL) and filtered to remove the undissolved solid. Removal of solvent provided 8.24 g (69.1% yield) of the title compound as a slightly yellowish powder, m.p.=318.1° C. (dec) ($R_f$=0.55 on a silica gel plate using 2:1 EtOAc/EtOH). This product consisted of 70% trans-isomer and 30% cis-isomer.

Spectroscopic data were as follows:

IR (KBr, $cm^{-1}$): 3423.1 (broad, hydrate and NH), 2960 (CH), 1662 and 1654 (C=O of two isomers), 1574 (furan ring), 1552 (NH), 1242.9 ($SO_2$, 1209.1 ($SO_2$), and 1045.0 ($SO_3$). $^1$H NMR ($D_2O$, 270 MHz): δ=7.157 (0.7H, d, J=15.6 Hz, vinyl CH of trans-isomer), 6.816–6.733 (1.3H, m, furan CH of trans-isomer and furan CH of cis-isomer), 6.657 (0.7H, d, J=3.5 Hz, furan CH of trans-isomer), 6.517 (0.3H, d, J=12.6 Hz, vinyl CH of cis-isomer), 6.430 (0.7H, d, J=15.6 Hz, vinyl CH of trans-isomer), 5.938 (0.3H, d, J=12.6 Hz, vinyl CH of cis-isomer) 3.153 (2H, m, $NCH_2$ of trans and cis isomers), 1.415 (2H, m, $CH_2$ of trans and cis isomers), 1.238 (2H, m, $CH_2$ of trans and cis isomers), and 0.813 (3H, t, J=7.3 Hz, $CH_3$ of trans and cis isomers). $^{13}$C NMR ($D_2O$, 270 MHz): δ=169.853, 168.297, 152.723, 152.540, 152.189, 151.854, 127.143, 123.116, 122.461, 120.767, 114.529, 113.766, 113.629, 39.269, 30.254, 29.980, 19.287, 19.195, and 12.698.

Example 6

Synthesis of 5-[2-(N-n-Butylcarbamoyl)ethyl]-furan-2-sulfonic Acid Sodium Salt

The title compound was prepared by hydrogenation of the product from Example 5 above using Pd/C at room temperature in ethanol in a Parr pressure reactor. The title compound was isolated in 28.8% yield as a solid, m.p.=184.9° C. (dec) ($R_f$=0.45 on a silica gel plate using 2:1 EtOAc/EtOH).

Spectroscopic data were as follows:

IR (KBr, cm$^{-1}$): 3432 (broad, hydrate & NH), 2960 (CH), 1637.2 (C=O), 1560.7 (NH), 1520.6 (furan ring), 1228.7 (SO$_2$), 1204.8 (SO$_2$), and 1044.5 (SO$_3$). $^1$H NMR (D$_2$O, 270 MHz): δ=6.727 (1H, d, J=3.3 Hz, furan CH), 6.182 (1H, d, J=3.3 Hz, furan CH), 3.087 (2H, t, J=6.7 Hz, NCH$_2$), 2.969 (2, t, J=6.9 Hz, CH$_2$), 2.563 (2H, t, J=6.9 Hz, CH$_2$CO), 1.340 (2H, m, CH$_2$), 1.183 (2H, m, CH$_2$), and 0.807 (3H, t, J=7.3 Hz, CH$_3$). $^{13}$C NMR (D$_2$O, 270 MHz): δ=175.069, 157.101, 150.435, 112.820, 107.375, 38.949, 33.854, 30.285, 23.832, 19.119, and 12.804.

Example 7

Synthesis of N-n-Butyl-5-(N-n-butylcarbamoyl) furan-2-sulfonamide

A suspension of 5-formyl-2-furansulfonic acid sodium salt (90 g, 0.454 mol) and potassium dichromate (89.1 g, 0.303 mol) in water (350 mL) was heated to reflux. With the heat off, a solution of sulfuric acid (98%, 55 mL) and water (50 mL) was added dropwise for 40 min. The reaction mixture was refluxed for an additional 3 hours and then cooled to room temperature. The pH of the reaction mixture was adjusted to about 10 with potassium hydroxide. After filtration, the filtrate was concentrated to ca. 200 mL. Chromatography of the residue on silica gel using methanol as the eluant gave 43.5 g of crude 5-carboxy-2-furansulfonic acid sodium/potassium salt.

A portion of salt (20.0 g, 79.3 mmol) was mixed with POCl$_3$ (40 mL) at 5–10° C. PCl$_5$ (40 g) was added in portions to the mixture. After stirred for 1 hour at room temperature, the mixture was filtered and the solid was washed with CH$_2$Cl$_2$. Rotary evaporation of the filtrate gave 14.8 g of crude 5-chlorocarbonyl-2-furansulfonyl chloride.

To a solution of this dichloride in CH$_2$Cl$_2$ (150 mL) was added dropwise a solution of n-butylamine (38 mL) in CH$_2$Cl$_2$ (50 mL) at 5–10° C. This mixture was stirred at room temperature for additional 18 hours and then poured into wet-ice (200 g). After conc. hydrochloric acid (6 mL) was added, the mixture was separated and the organic layer was washed with water (2×200 mL). The solution was dried over sodium sulfate, filtered and evaporated. Removal of solvent provided the title compound (8.42 g, 13.3% overall yield) as a solid, m.p.=69.4° C. ($R_f$=0.63 on a silica gel plate using EtOAc as an eluant).

Spectroscopic data were as follows:

IR (KBr, cm$^{-1}$): 3382.9 (NH), 2962 (CH), 2934 (CH), 2872 (CH), 1656.0 (C=O), 1596.6 (furan ring), 1539.7 (NH), 1340.7 (SO$_2$) and 1183.3 (SO$_2$). $^1$H NMR (CDCl$_3$, 270 MHz): δ=7.123 (1H, d, J=3.6 Hz, furan CH), 7.045 (1H, d, J=3.6 Hz, furan CH), 6.576 (1H, t, J=5.2 Hz, COHN), 5.098 (1H, t, J=5.9 Hz, NHSO$_2$), 3.398 (2H, q, J=6.8 Hz, CH$_2$), 3.030 (2H, q, J=6.7 Hz, CH$_2$), 1.620–1.216 (8H, m, 2 CH$_2$CH$_2$), 0.923 (3H, t, J=7.3 Hz, CH$_3$) and 0.848 (3H, t, J=7.2 Hz, CH$_3$). $^{13}$C NMR (CDCl$_3$, 270 MHz): δ=157.437, 150.725, 149.215, 117.534, 114.437, 42.853, 38.933, 31,230, 19.668, 19.195, 13.262 and 13.033.

Example 8

Synthesis of N,N-Diethyl-5-(N,N-diethylcarbamoyl) furan-2-sulfonamide

The procedure described in Example 7 was employed for the preparation of the title compound using diethylamine instead of n-butylamine. The title compound was separated in 5.9% overall yield as a solid, m.p. 56.4° C. ($R_f$=0.22 on a silica gel plate using EtOAc/hexanes, 1: 1, v:v, as the eluant).

Spectroscopic data were as follows:

IR (KBr, cm$^{-1}$): 2978 (CH), 2938 (CH), 1631.3 (C=O), 1571.6 (furan ring), 1360.6 (SO$_2$) and 1171.0 (SO$_2$). $^1$H NMR (CDCl$_3$, 270 MHz): δ=7.004 (1H, d, J=3.6 Hz, furan CH), 6.958 (1H, d, J=3.6 Hz, furan CH), 3.499 (4H, broad m, 2 CH$_2$), 3.289 (4H, q, J=7.2 Hz, 2 CH$_2$), 1.224 (6H, broad m, 2 CH$_3$) and 1.145 (6H, t, J=7.2 Hz, 2 CH$_3$). $^{13}$C NMR (CDCl$_3$, 270 MHz): δ=158.825, 151.228, 149.840, 116.130, 42.609, 42.198, 14.421, 13.857 and 112.225.

Using the procedures described in Examples 1–8 above and the appropriate starting materials and reagents, the following additional furansulfonic acid derivatives of formula I can be prepared:

N-methyl-5-carbamoylfuran-2-sulfonic acid
N-ethyl-5-carbamoylfuran-2-sulfonic acid
N-n-propyl-5-carbamoylfuran-2-sulfonic acid
N-isobutyl-5-carbamoylfuran-2-sulfonic acid
N-sec-butyl-5-carbamoylfuran-2-sulfonic acid
N-tert-butyl-5-carbamoylfuran-2-sulfonic acid
N-n-pentyl-5-carbamoylfuran-2-sulfonic acid
N-cyclopentyl-5-carbamoylfuran-2-sulfonic acid
N-n-hexyl-5-carbamoylfuran-2-sulfonic acid
N-n-octyl-5-carbamoylfuran-2-sulfonic acid
N-tert-octyl-5-carbamoylfuran-2-sulfonic acid
N-phenyl-5-carbamoylfuran-2-sulfonic acid
5-(1-pyrrolidinylcarbonyl)furan-2-sulfonic acid 5-(4-morpholinylcarbonyl)furan-2-sulfonic acid
N-methyl-4-carbamoylfuran-2-sulfonic acid
N-ethyl-4-carbamoylfuran-2-sulfonic acid
N-n-propyl-4-carbamoylfuran-2-sulfonic acid
N-isopropyl-4-carbamoylfuran-2-sulfonic acid
N-n-butyl-4-carbamoylfuran-2-sulfonic acid
N-isobutyl-4-carbamoylfuran-2-sulfonic acid
N-sec-butyl-4-carbamoylfuran-2-sulfonic acid
N-tert-butyl-4-carbamoylfuran-2-sulfonic acid
N-n-pentyl-4-carbamoylfuran-2-sulfonic acid
N-cyclopentyl-4-carbamoylfuran-2-sulfonic acid
N-n-hexyl-4-carbamoylfuran-2-sulfonic acid
N-cyclohexyl-4-carbamoylfuran-2-sulfonic acid
N-n-octyl-4-carbamoylfuran-2-sulfonic acid
N-ter-octyl4-carbamoylfuran-2-sulfonic acid
N-phenyl-4-carbamoylfuran-2-sulfonic acid
4-(1-piperidylcarbonyl)furan-2-sulfonic acid
4-(1-pyrrolidinylcarbonyl)furan-2-sulfonic acid
4-(4-morpholinylcarbonyl)furan-2-sulfonic acid
N,N-dimethyl-5-carbamoylfuran-2-sulfonic acid
N,N-diethyl-5-carbamoylfuran-2-sulfonic acid
N,N-di-n-propyl-5-carbamoylfuran-2-sulfonic acid
N,N-diisopropyl-5-carbamoylfuran-2-sulfonic acid
N,N-di-n-butyl-5-carbamoylfuran-2-sulfonic acid
N,N-diisobutyl-5-carbamoylfuran-2-sulfonic acid
N,N-di-sec-butyl-5-carbamoylfuran-2-sulfonic acid
N-ethyl-n-methyl-5-carbamoylfuran-2-sulfonic acid
N-n-propyl-N-methyl-5-carbamoylfuran-2-sulfonic acid
N-isopropyl-N-methyl-5-carbamoylfuran-2-sulfonic acid N-n-butyl-N-methyl-5-carbamoylfuran-2-sulfonic acid N-cyclohexyl-N-methyl-5-carbamoylfuran-2-sulfonic acid N-ethyl-N-n-propyl-5-carbamoylfuran-2-sulfonic acid N-ethyl-N-isopropyl-5-carbamoylfuran-2-sulfonic acid N-ethyl-N-n-butyl-5-carbamoylfuran-2-sulfonic acid N-ethyl-N-cyclohexyl-5-carbamoylfuran-2-sulfonic acid 5-[2-(N-methylcarbamoyl)eth-1-enyl]furan-2-sulfonic acid 5-[2-(N-ethylcarbamoyl)eth-1-enyl]furan-2-sulfonic acid 5-[2-(N-n-propylcarbamoyl)eth-1-enyl]furan-2-sulfonic acid 5-[2-(N-isopropylcarbamoyl)eth-1-enyl]furan-2-sulfonic acid 5-[2-(N-isobutylcarbamoyl)eth-1-enyl]furan-2-sulfonic acid 5-[2-(N-tert-butylcarbamoyl)eth-1-enyl]furan-2-sulfonic acid 5-[2-(N-cyclohexylcarbamoyl)eth-1-enyl]furan-2-sulfonic acid 5-[2-(N,-dimethylcarbamoyl)eth-1-enyl]furan-2-sulfonic acid 5-[2-(N-methylcarbamoyl)ethyl]furan-2-sulfonic acid 5-[2-(N-ethylcarbamoyl)ethyl]furan-2-sulfonic acid 5-[2-(N-n-propylcarbamoyl)ethyl]furan-2-sulfonic acid 5-[2-(N-isopropylcarbamoyl)ethyl]furan-2-sulfonic acid 5-[2-(N-isobutylcarbamoyl)ethyl]furan-2-sulfonic acid 5-[2-(N-tert-butylcarbamoyl)ethyl]furan-2-sulfonic acid 5-[2-(N-cyclohexylcarbamoyl)ethyl]furan-2-sulfonic acid 5-[2-(N,N-dimethylcarbamoyl)ethyl]furan-2-sulfonic acid N-methyl-5-(N-methylcarbamoyl)furan-2-sulfonamide N-ethyl-5-(N-ethylcarbamoyl)furan-2-sulfonamide N-n-propyl-5-(N-n-propylcarbamoyl)furan-2-sulfonamide N-iso-propyl-5-(N-iso-propylcarbamoyl)furan-2-sulfonamide N-tertbutyl-5-(N-tert-butylcarbamoyl)furan-2-sulfonamide N-cyclopentyl-5-(N-cyclopentylcarbamoyl)furan-2-sulfonamide N-n-hexyl-5-(N-n-hexylcarbamoyl)furan-2-sulfonamide N-cyclohexyl-5-(N-cyclohexylcarbamoyl)furan-2-sulfonamide, and the like; and pharmaceutically acceptable salts thereof.

Example 9

Inhibition of Aβ(1-40) Beta-Pleated Sheet Formation

Thioflavin T (ThT) is known to rapidly associate with beta-pleated sheets, particularly the aggregated fibrils of synthetic Aβ(1-40). This association gives rise to a new excitation maximum at 440 nm and to enhanced emission at 490 nm. In this experiment, the ability of the compounds prepared in Examples 1, 2 and 6 above to inhibit the association of ThT with synthetic Aβ(1-40) is demonstrated by measuring changes in fluorescence.

The experiments were performed using a CytoFluor II fluorescence plate reader having the following parameters:

| Filters: | Excitation 440 nm/20 |
| | Emission 490 nm/40 |
| Gain: | 75 |
| Cycle to Cycle Time: | 30 min |
| Run Time: | 720 min (24 cycles) of dependent on experimental design |
| Plate: | 96 well |

Into each well was aliquoted 95 μl of ThT (3 μM) prepared in PBS (pH 6.0), 2 μL of the compound to be tested (10 μM) prepared with 0.05% of methylcellulose in PBS (pH 6.0), and 3 μL of Aβ(1-40) (3 μg) prepared with $dH_2O$. The fluorescence measurement began when the Aβ(1-40) was added and continued for a total of 12–24 hours. The percent inhibition of beta-pleated sheet formation was calculated from the relative fluorescence unit increase over the 12–24 hours between aggregation in the presence and in the absence of the test compounds. The data show that the compounds prepared in Examples 1, 2 and 6 above inhibited Aβ(1-40) beta-pleated sheet formation at least 10% compared to the controls.

Example 10

Protection Against Aβ(25-35)-Induced Neuronal Cell Loss

In this experiment, the ability of the compounds prepared in Examples 1, 2 and 5 above to protect against Aβ(25-35)-induced neuronal cell loss is demonstrated. Sprague Dawley rat hippocampus of 18-day-gestation embryos was excised and then dissociated by trituration to prepare primary neuronal/astrocytic cultures. Cells ($3 \times 10^5$) were plated on 35 mm poly-D-lysine-coated plates containing Eagle's minimum essential medium supplemented with 10% fetal bovine serum. After 3–5 hours, the original medium was removed and replaced with 1 mL of fresh medium. Cultures were maintained at 37° C. in a 5% $CO_2$/95% air, humidified incubator.

To the cells (7 DIV) was added 30 μM of Aβ(25-35) dissolved in $dH_2O$ (stored at −20° C.) and 100 μM of the test compound in 1% methylcellulose. Controls were also conducted without the test compound. The percentage of morphologically viable neurons was determined counting the number of viable neurons after 96 hours treatment compared to the number of neurons before treatment in the same premarked culture regions (three regions/culture). The number of wells was n=6 per treatment condition. The data show that the compounds prepared in Example 1, 2 and 5 above reduce Aβ(25-35)-induced neuronal cell loss by at least 60% compared to the controls.

Example 11

Reduction of β-Amyloid-Induced Increased Release of Interleukin-1β, Interleukin-6 and Tumor Necrosis Factor-α

In this experiment, the ability of the compounds prepared in Examples 1, 2, 5 and 6 above to reduce the LPS and β-amyloid-induced increased release of interleukin-1β (IL-1β), interleukin-6 (IL-6) and tumor necrosis factor-α (TNFα) is demonstrated. THP-1 cells, a human monocyte cell line from American Type Culture Collection, were grown in RPMI-1640 medium plus 10% fetal bovine serum (FBS, not heat-inactivated) in T-flasks. The medium was changed every two days by spinning down (800 rpm, 5 minutes) the cells, replating cells and adding fresh medium. Alternatively, the cultures were maintained by the addition of fresh medium. The cultures were maintained at a cell concentration ranging from between $1 \times 10^5$ and $1 \times 10^6$ cells/mL. Because sera may contain unknown factors which can affect macrophage/monocyte IL-1 production, the FBS was reduced to 5% for 24 hours. The FBS was further reduced to 2% over two days prior to starting each experiment. The cells were collected by centrifugation and resuspended into 2% FBS. Cell numbers were calculated and cells were plated on 24-well plates ($3 \times 10^5$ cells/0.6 mL/well). Cells were then treated with LPS (0.5 μg/ml or 0–10 μg/ml for LPS dose-response experiments) alone or in combination with Aβ peptides (5 μM or 0.05–5 μM for dose-response experiments). When determining the effect of the test compounds on IL-1β, IL-6 and TNFα release, 100 μM of the test compound was added with the LPS and Aβ(25-35) and this mixture was incubated for 48 hours prior to performing ELISA.

IL-1β, IL-6 and TNFα secretions into medium by LPS-stimulated THP-1 cells, in the presence or absence of amyloid peptides and a test compound, were assayed with a commercially available ELISA kit (R & D Systems). Briefly, a microtiter plate coated with a murine monoclonal antibody to human IL-1β, IL-6, or TNFα was supplied by the manufacturer. Standards and samples were pipetted into the wells and any IL-1β, IL-6 or TNFα present was bound by the immobilized antibody. Unbound proteins were washed away and a horseradish peroxidase-linked polyclonal antibody specific for IL-1β, IL-6 or TNFα was added to the wells to "sandwich" the IL-1β, IL-6 and TNFα bound in the initial step. After washing to remove any unbound antibody-enzyme reagent, a substrate solution (1:1 hydrogen peroxide:tetramethylbenzidine, v/v) was added to the wells and color developed in proportion to the amount of IL-1β, IL-6 or TNFα bound in the initial step. Color development was stopped with 2 N sulfuric acid and the optical density of the standard and the test samples was measured at 450 nm. The amounts of IL-1β, IL-6 or TNFα present in the samples were calculated based upon a standard curve. Assays were run in quadruplicate wells. The data show that the compounds prepared in Example 1, 2, 5 and 6 above reduced the β-amyloid-induced increased release of interleukin-1β, interleukin-6 and tumor necrosis factor-α by at least 20% compared to the controls.

Example 12

Reduction of Locomotor Impairment Due to Aβ-Peptide

In this experiment, the ability of the compound prepared in Example 1 above to reduce the in vivo impairment of animals treated with Aβ-peptide is demonstrated. Male Sprague-Dawley rats (250–400 g) were given injections of 20 μg of Aβ(25-35) into their substantia nigra. Prior to the injection, the rats were fasted overnight and then each received an oral treatment of the test compound (1–10 mg/kg) dissolved in aqueous 1% methyl cellulose or the vehicle alone, one hour before and three hours post the Aβ-peptide stereotaxic injection. One week after treatment, the rats were dosed s.c. with 0.5 mg/kg apomorphine (dissolved in 0.1% vitamin C in isotonic saline) and the circling reflex was monitored using a Rotorat computerized behavioral monitoring apparatus for the time period between 15 and 30 minutes of being placed in the arena. Impairment of the animals due to Aβ-peptide was determined by measuring the number of rotations over the 15 minute period.

The data show that the compound of Example 1 above reduced the locomotor impairment of rats injected with Aβ(25-35) compared to AP(25-35)-treated controls.

Example 13

Reduction of Cognitive Deficits in Autoimmune Mice

In this experiment, the ability of the compound prepared in Example 1 above to reduce cognitive deficits in autoimmune strains of mice is demonstrated. MRL/MpJfas$^{1pr}$ ("mutant mice" or "Fas$^{1pr}$") strains of mice have been described as useful models of Lupus due to their autoimmune lymphoproliferative pathology. In particular, the mutant mice show a cognitive deficit at approximately four months of age, which is not observed at two months of age. See, for example, Forster et al., 1988, Behav. Neural Biology, 49, 139–151.

Figure 2:
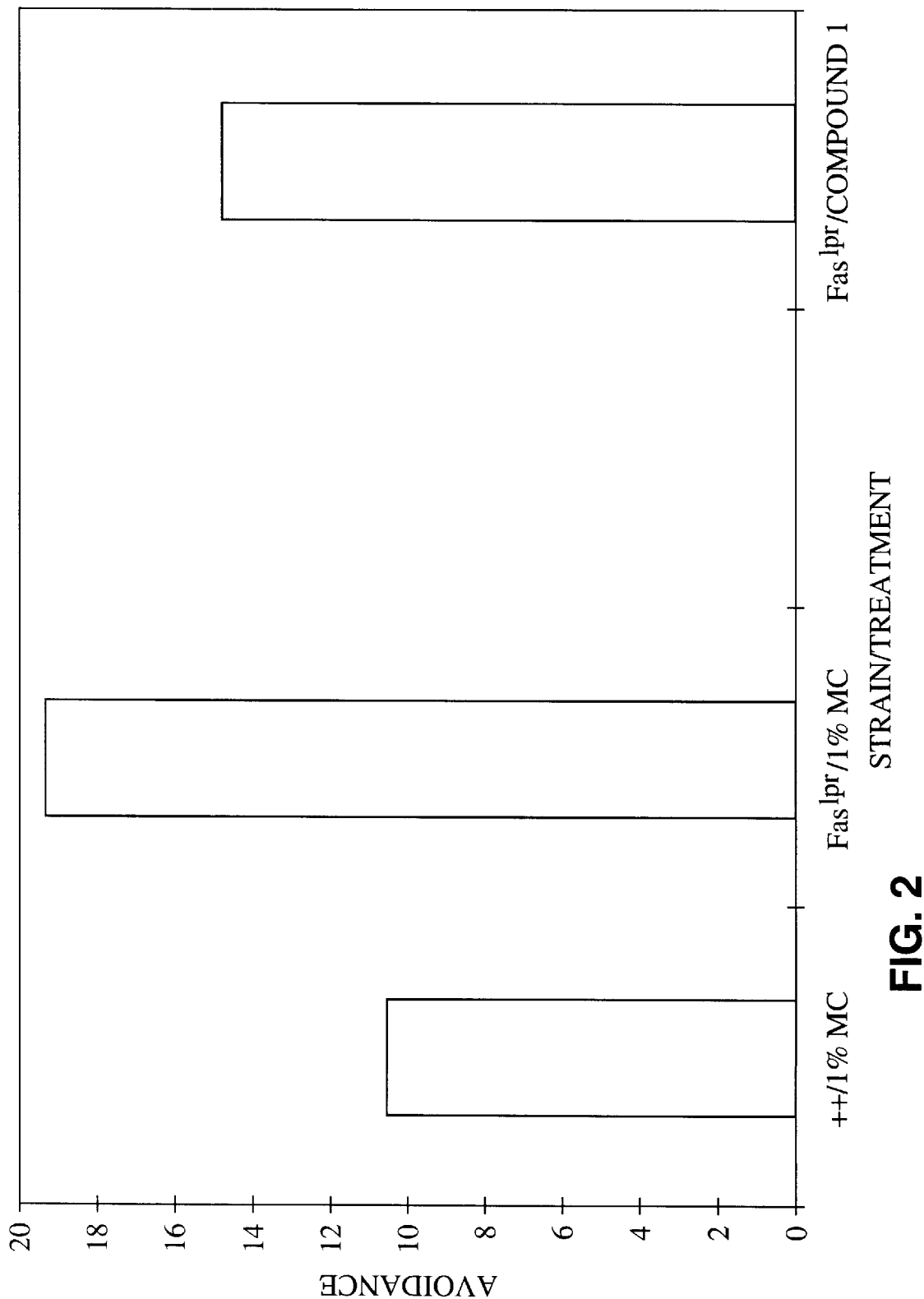
FIG. 2 is a bar graph illustrating the avoidance scores for wild-type mice ("++") treated with 1% methylcellulose ("MC"), and $Fas^{lpr}$ strains of mice treated with 1% methylcellulose or 100 mg/kg of N-n-butyl-5-carbamoylfuran-2-sulfonic acid sodium salt ("Compound 1").

In the experiment, wild-type ("++") and Fas$^{1pr}$ strains of mice were received at 4 to 8 weeks of age (n=10–11). The compound of Example 1 above or 1% methylcellulose (100 mg/kg p.o.) was administered daily from 2 months of age to 4 months of age (a total of 9 weeks). After reaching 4 months of age, the mice were tested for cognitive ability in a T-maze. This behavioral task measures discrimination, active avoidance and acquisition skills (acquisition is the number of avoidances in the first 5 test trials). The Fas$^{1pr}$ mice showed a deficit in both avoidance and acquisition compared to the wild-type mice which received the 1% methylcellulose. In contrast, the Fas$^{1pr}$ mice treated with the compound of Example 1 above had reduced avoidance values and acquired avoidance skills earlier than untreated mutant mice (i.e., similar to the wild-type controls). The data for acquisition and avoidance are shown in FIGS. 1 and 2, respectively. These results demonstrate that the compound prepared in Example 1 above reduced the cognitive deficits of the autoimmune mutant strain of mice.

From the foregoing description, various modifications and changes in the compositions and methods of this invention will occur to those skilled in the art. All such modifications coming within the scope of the appended claims are intended to be included therein.

What is claimed is:

1. A compound of formula I:

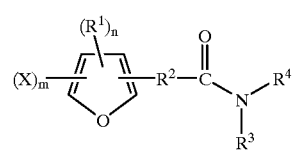

I wherein
each $R^1$ is independently selected from the group consisting of hydrogen, alkyl, alkenyl, alkynyl, alkaryl, aryl, alkoxy, alkcycloalkyl, cycloalkyl, cycloalkenyl and halo;

$R^2$ is selected from the group consisting of alkylene, alkenylene and a covalent bond;

$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur, wherein said heterocyclic ring is selected from the group consisting of morpholinyl, piperazinyl and imidazolidinyl;

each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

m is an integer from 1 to 3; and n is an integer from 0 to 2, provided that m+n=3.

2. The compound according to claim 1 wherein $R^1$ is hydrogen.

3. The compound according to claim 1 wherein $R^1$ is selected from the group consisting of an alkylene group of the formula —$(CH_2)_p$—, wherein p is an integer from 1 to 6; an alkenylene group of the formula —$CR^7$=$CR^8$—, wherein $R^7$ and $R^8$ are independently selected from the group consisting of hydrogen and lower alkyl; and a covalent bond.

4. The compound according to claim 3 wherein $R^2$ is selected from the group consisting of —$CH_2CH_2$—, —CH=CH— and a covalent bond.

5. The compound according to claim 1 wherein $R^3$ and $R^4$ are independently selected from the group consisting of hydrogen, alkyl and cycloalkyl, provided that $R^3$ and $R^4$ are not both hydrogen; or $R^3$ and $R^4$ are joined together to form a cycloalkyl group having 4 or 6 carbon atoms.

6. The compound according to claim 5 wherein $R^3$ is hydrogen and $R^4$ is lower alkyl or cycloalkyl.

7. The compound according to claim 1 wherein X is —$SO_3Y$.

8. The compound according to claim 1 wherein X is —$SO_2NR^5R^6$, wherein $R^5$ and $R^6$ are independently selected from the group consisting of hydrogen, alkyl and cycloalkyl; or $R^5$ and $R^6$ are joined together to form a cycloalkyl ring having 4 to 6 carbon atoms.

9. The compound according to claim 8 wherein $R^5$ is hydrogen and $R^6$ is selected from the group consisting of hydrogen, alkyl and cycloalkyl.

10. The compound according to claim 1 wherein m is 1.

11. A compound of formula II or III:

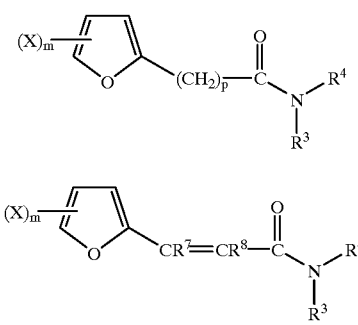

wherein $R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur wheren in the compounds of formula II said heterocyclic ring is selected from the group consisting of morpholinyl, piperazinyl and imidazolidinyl;;

each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

$R^7$ and $R^8$ are independently selected from the group consisting of hydrogen and lower alkyl;

m is an integer from 1 to 3; and p is an integer from 0 to 6.

12. The compound according to claim 11 wherein $R^3$ and $R^4$ are independently selected from the group consisting of hydrogen, alkyl and cycloalkyl, provided that $R^3$ and $R^4$ are not both hydrogen; or $R^3$ and $R^4$ are joined together to form a cycloalkyl group having 4 or 6 carbon atoms.

13. The compound according to claim 12 wherein $R^3$ is hydrogen and $R^4$ is lower alkyl or cycloalkyl.

14. The compound according to claim 11 wherein X is —$SO_3Y$.

15. The compound according to claim 11 wherein $R^7$ and $R^8$ are hydrogen.

16. The compound according to claim 11 wherein p is 0, 1 or 2.

17. The compound according to claim 11 wherein m is 1.

18. A compound of formula IV:

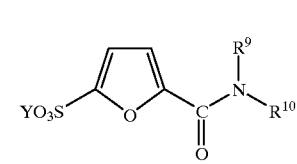

wherein $R^9$ and $R^{10}$ are independently selected from the group consisting of hydrogen, lower alkyl and cycloalkyl, provided that $R^9$ and $R^{10}$ are not both hydrogen; or $R^9$ and $R^{10}$ are joined together to form a cycloalkyl ring having 4 to 6 carbon atoms; and Y is selected from the group consisting of hydrogen and a pharmaceutically acceptable cation.

19. The compound according to claim 18 wherein Y is hydrogen or a sodium cation.

20. A compound of formula V:

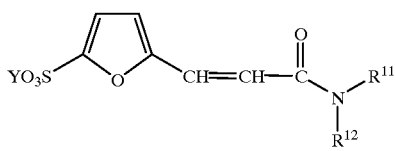

wherein
R$^{11}$ and R$_{12}$ are independently selected from the group consisting of hydrogen, lower alkyl and cycloalkyl, provided that R$^{11}$ and R$^{12}$ are not both hydrogen; or R$^{11}$ and R$^{12}$ are joined together to form a cycloalkyl ring having 4 to 6 carbon atoms; and Y selected from the group consisting of hydrogen and a pharmaceutically acceptable cation.

21. The compound according to claim 20 wherein Y is hydrogen or a sodium cation.

22. A compound of formula VI:

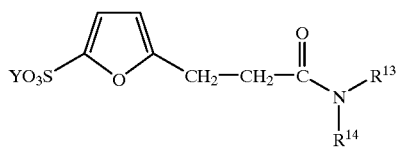

wherein
R$^{13}$ and R$^{14}$ are independently selected from the group consisting of hydrogen, lower alkyl and cycloalkyl, provided that R$^{13}$ and R$^{14}$ are not both hydrogen; or R$^{13}$ and R$^{14}$ are joined together to form a cycloalkyl ring having 4 to 6 carbon atoms; and Y selected from the group consisting of hydrogen and a pharmaceutically acceptable cation.

23. The compound according to claim 22 wherein Y is hydrogen or a sodium cation.

24. A compound selected from the group consisting of:
N-n-butyl-5-carbamoylfuran-2-sulfonic acid
N-isopropyl-5-carbamoylfuran-2-sulfonic acid
N-cyclohexyl-5-carbamoylfuran-2-sulfonic acid
5-(1-piperidylcarbonyl)furan-2-sulfonic acid
5-[2-(N-n-butylcarbamoyl)eth-1-enyl]furan-2-sulfonic acid
5-[2-(N-n-butylcarbamoyl)ethyl]furan-2-sulfonic acid
N-n-butyl-5-(N-n-butylcarbamoyl)furan-2-sulfonamide
N,N-diethyl-5-(N,N-diethylcarbamoyl)furan-2-sulfonamide,
and pharmaceutically acceptable salts thereof.

25. The compound according to claim 24 wherein the compound is selected from the group consisting of N-n-butyl-5-carbamoylfuran-2-sulfonic acid and pharmaceutically acceptable salts thereof.

26. The compound according to claim 24 wherein the compound is selected from the group consisting of N-isopropyl-5-carbamoylfuran-2-sulfonic acid and pharmaceutically acceptable salts thereof.

27. The compound according to claim 24 wherein the compound is selected from the group consisting of N-cyclohexyl-5-carbamoylfuran-2-sulfonic acid and pharmaceutically acceptable salts thereof.

28. The compound according to claim 24 wherein the compound is selected from the group consisting of 5-(1-piperidylcarbonyl)furan-2-sulfonic acid and pharmaceutically acceptable salts thereof.

29. The compound according to claim 24 wherein the compound is selected from the group consisting of 5-[2-(N-n-butylcarbamoyl)eth-1-enyl]furan-2-sulfonic acid and pharmaceutically acceptable salts thereof.

30. The compound according to claim 24 wherein the compound is selected from the group consisting of 5-[2-(N-n-butylcarbamoyl)ethyl]furan-2-sulfonic acid and pharmaceutically acceptable salts thereof.

31. The compound according to claim 24 wherein the compound is selected from the group consisting of N,N-diethyl-5-(N,N-diethylcarbamoyl)furan-2-sulfonamide and pharmaceutically acceptable salts thereof.

32. A pharmaceutical composition comprising a pharmaceutically acceptable carrier and a pharmaceutically effective amount of a compound of formula I:

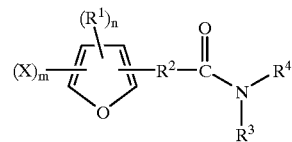

wherein
each R$^1$ is independently selected from the group consisting of hydrogen, alkyl, alkenyl, alkynyl, alkaryl, aryl, alkoxy, alkcycloalkyl, cycloalkyl, cycloalkenyl and halo;

R$^2$ is selected from the group consisting of alkylene, alkenylene and a covalent bond;

R$^3$ and R$^4$ are independently selected from the group consisting of hydrogen, alkyl, alkenyl, alkynyl, alkaryl, aryl, alkoxy, alkcycloalkyl, cycloalkyl and cycloalkenyl, provided that R$^3$ and R$^4$ are not both hydrogen; or R$^3$ and R$^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur, wherein said heterocyclic ring is selected from the group consisting of morpholinyl, piperazinyl and imidazolidinyl;

each X is independently selected from the group consisting of —SO$_3$Y and —SO$_2$NR$^5$R$^6$, wherein Y is hydrogen or a pharmaceutically acceptable cation, and R$^5$ and R$^6$ are independently selected from the group consisting of hydrogen, alkyl, alkenyl, alkynyl, alkaryl, aryl, alkoxy, alkcycloalkyl, cycloalkyl and cycloalkenyl; or R$^5$ and R$^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

m is an integer from 1 to 3; and n is an integer from 0 to 2, provided that m+n=3.

33. The pharmaceutical composition according to claim 32 wherein R$^1$ is hydrogen.

34. The pharmaceutical composition according to claim 32 wherein R$^2$ is selected from the group consisting of an alkylene group of the formula —(CH$_2$)$_p$—, wherein p is an integer from 1 to 6; an alkenylene group of the formula —CR$^7$=CR$^8$—, wherein R$^7$ and R$^8$ are independently selected from the group consisting of hydrogen and lower alkyl; and a covalent bond.

35. The pharmaceutical composition according to claim 34 wherein $R^2$ is selected from the group consisting of —$CH_2CH_2$—, —CH=CH— and a covalent bond.

36. The pharmaceutical composition according to claim 32 wherein $R^3$ and $R^4$ are independently selected from the group consisting of hydrogen, alkyl and cycloalkyl, provided that $R^3$ and $R^4$ are not both hydrogen; or $R^3$ and $R^4$ are joined together to form a cycloalkyl group having 4 or 6 carbon atoms.

37. The pharmaceutical composition according to claim 36 wherein $R^3$ is hydrogen and $R^4$ is lower alkyl or cycloalkyl.

38. The pharmaceutical composition according to claim 32 wherein X is —$SO_3Y$.

39. The pharmaceutical composition according to claim 32 wherein X is —$SO_2NR^5R^6$, wherein $R^5$ and $R^6$ are independently selected from the group consisting of hydrogen, alkyl and cycloalkyl; or $R^5$ and $R^6$ are joined together to form a cycloalkyl ring having 4 to 6 carbon atoms.

40. The pharmaceutical composition according to claim 39 wherein $R^5$ is hydrogen and $R^6$ is selected from the group consisting of hydrogen, alkyl and cycloalkyl.

41. The pharmaceutical composition according to claim 32 wherein m is 1.

42. The pharmaceutical composition according to claim 32 wherein the carrier is an oral carrier.

43. The pharmaceutical composition according to claim 32 wherein the carrier is an injectable carrier.

44. A method for treating a patient with a neurodegenerative disease which method comprises administering to said patient a pharmaceutical composition comprising a pharmaceutically acceptable carrier and an effective neurodegenerative disease-treating amount of a compound of formula I:

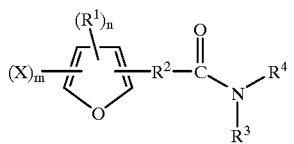

wherein
  each $R^1$ is independently selected from the group consisting of hydrogen, alkyl, alkenyl, alkynyl, alkaryl, aryl, alkoxy, alkcycloalkyl, cycloalkyl, cycloalkenyl and halo;
  $R^2$ is selected from the group consisting of alkylene, alkenylene and a covalent bond;
  $R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
  each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
  m is an integer from 1 to 3; and n is an integer from 0 to 2, provided that m+n=3.

45. A method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a compound of formula I:

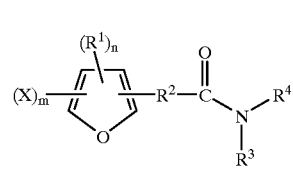

wherein
  each $R^1$ is independently selected from the group consisting of hydrogen, alkyl, alkenyl, alkynyl, alkaryl, aryl, alkoxy, alkcycloalkyl, cycloalkyl, cycloalkenyl and halo;
  $R^2$ is selected from the group consisting of alkylene, alkenylene and a covalent bond;
  $R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
  each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
  m is an integer from 1 to 3; and n is an integer from 0 to 2, provided that m+n=3.

46. The method according to claim 44 or 45 wherein the neurodegenerative disease is Alzheimer's disease.

47. The method according to claim 44 or 45 wherein the neurodegenerative disease is Parkinson's disease.

48. The method according to claim 44 or 45 wherein the neurodegenerative disease is HIV dementia.

49. A method for treating a patient with an autoimmune disease which method comprises administering to said patient a pharmaceutical composition comprising a pharmaceutically acceptable carrier and an effective autoimmune disease-treating amount of a compound of formula I:

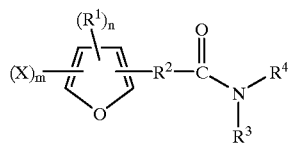

wherein
- each $R^1$ is independently selected from the group consisting of hydrogen, alkyl, alkenyl, alkynyl, alkaryl, aryl, alkoxy, alkcycloalkyl, cycloalkyl, cycloalkenyl and halo;
- $R^2$ is selected from the group consisting of alkylene, alkenylene and a covalent bond;
- $R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur, wherein said heterocyclic ring is selected from the group consisting of morpholinyl, piperazinyl and imidazolidinyl;
- each X is independently selected from the group consisting of $-SO_3Y$ and $-SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
- m is an integer from 1 to 3; and n is an integer from 0 to 2, provided that m+n=3.

50. A method for preventing the onset of an autoimmune disease in a patient at risk for developing the autoimmune disease which method comprises administering to said patient a pharmaceutical composition comprising a pharmaceutically acceptable carrier and an effective autoimmune disease-preventing amount of a compound of formula I:

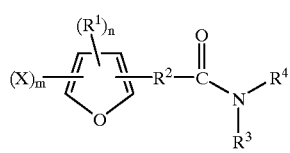

wherein
- each $R^1$ is independently selected from the group consisting of hydrogen, alkyl, alkenyl, alkynyl, alkaryl, aryl, alkoxy, alkcycloalkyl, cycloalkyl, cycloalkenyl and halo;
- $R^2$ is selected from the group consisting of alkylene, alkenylene and a covalent bond;
- $R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur, wherein said heterocyclic ring is selected from the group consisting of morpholinyl, piperazinyl and imidazolidinyl;
- each X is independently selected from the group consisting of $-SO_3Y$ and $-SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
- m is an integer from 1 to 3; and n is an integer from 0 to 2, provided that m+n=3.

51. The method according to claim 49 or 50 wherein the autoimmune disease is systemic lupus.

52. A method for treating a patient with an inflammatory disease which method comprises administering to said patient a pharmaceutical composition comprising a pharmaceutically acceptable carrier and an effective inflammatory disease-treating amount of a compound of formula I:

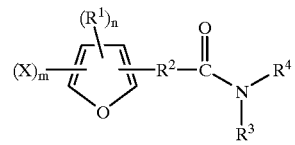

wherein
- each $R^1$ is independently selected from the group consisting of hydrogen, alkyl, alkenyl, alkynyl, alkaryl, aryl, alkoxy, alkcycloalkyl, cycloalkyl, cycloalkenyl and halo;
- $R^2$ is selected from the group consisting of alkylene, alkenylene and a covalent bond;
- $R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur, wherein said heterocyclic ring is selected from the group consisting of morpholinyl, piperazinyl and imidazolidinyl;
- each X is independently selected from the group consisting of $-SO_3Y$ and $-SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from I to 3 heteroatoms selected from the group consisting of oxygen, nitrogen and sulfur;
- m is an integer from 1 to 3; and n is an integer from 0 to 2, provided that m+n=3.

53. A method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a compound of formula I:

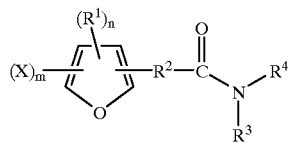

wherein
each $R^1$ is independently selected from the group consisting of hydrogen, alkyl, alkenyl, alkynyl, alkaryl, aryl, alkoxy, alkcycloalkyl, cycloalkyl, cycloalkenyl and halo;
$R^2$ is selected from the group consisting of alkylene, alkenylene and a covalent bond;
$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur, wherein said heterocyclic ring is selected from the group consisting of morpholinyl, piperazinyl and imidazolidinyl;
each X is independently selected from the group consisting of $—SO_3Y$ and $—SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
m is an integer from 1 to 3; and n is an integer from 0 to 2, provided that m+n=3.

54. The method according to claim 52 or 53 wherein the inflammatory disease is rheumatoid arthritis.
55. The method according to claim 52 or 53 wherein the inflammatory disease is septic shock.
56. The method according to claim 52 or 53 wherein the inflammatory disease is erythema nodosum leprosy.
57. The method according to claim 52 or 53 wherein the inflammatory disease is septicemia.
58. The method according to claim 52 or 53 wherein the inflammatory disease is uveitis.
59. The method according to claim 52 or 53 wherein the inflammatory disease is adult respiratory distress syndrome.
60. The method according to claim 52 or 53 wherein the inflammatory disease is multiple sclerosis.
61. A process for preparing a carbamoyl-substituted furansulfonic acid of formula I':

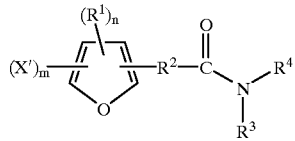

wherein
each $R^1$ is independently selected from the group consisting of hydrogen, alkyl, alkenyl, alkynyl, alkaryl, aryl, alkoxy, alkcycloalkyl, cycloalkyl, cycloalkenyl and halo;

$R^2$ is selected from the group consisting of alkylene, alkenylene and a covalent bond;
$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;
each X' is $—SO_3Y$, wherein Y is hydrogen or a pharmaceutically acceptable cation;
m is an integer from 1 to 3; and n is an integer from 0 to 2, provided that m+n=3; said process comprising the steps of:
(a) reacting a furan carboxylic acid halide of the formula:

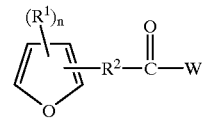

wherein $R^1$, $R^2$ and n are as defined above and W is chloro or bromo, with an amine of the formula:

wherein $R^3$ and $R^4$ are as defined above, to provide a furan carboxamide of the formula:

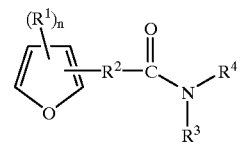

and
(b) reacting the furan carboxamide with a sulfonating reagent to provide the carbamoyl-substituted furan sulfonic acid.
62. The process according to claim 61 wherein the sulfonating reagent is sulfur trioxide pyridine complex.
63. A compound of formula I:

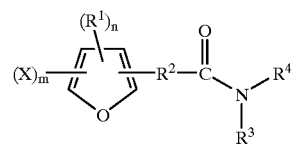

wherein
each $R^1$ is independently selected from the group consisting of hydrogen, alkyl, alkenyl, alkynyl, alkaryl, aryl, alkoxy, alkcycloalkyl, cycloalkyl, cycloalkenyl and halo;
$R^2$ is selected from the group consisting of alkylene, alkenylene and a covalent bond;
$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

m is an integer from 1 to 3; and n is an integer from 0 to 2, provided that m+n=3;

provided that when m is 1, n is 2, X is 4-sulfo, each $R^1$ is hydrogen and $R^2$ is a covalent bond, then $R^3$ and $R^4$ are not joined to form a 6-methoxycarbonyl-1,1,3-trioxo-1,2-benzisothiazol-2-yl or 1,1,3-trioxo-1,2-benzisothiazol-2-yl group.

64. A pharmaceutical composition comprising a pharmaceutically acceptable carrier and a pharmaceutically effective amount of a compound of formula I:

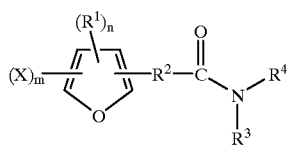

wherein each $R^1$ is independently selected from the group consisting of hydrogen, alkyl, alkenyl, alkynyl, alkaryl, aryl, alkoxy, alkcycloalkyl, cycloalkyl, cycloalkenyl and halo;

$R^2$ is selected from the group consisting of alkylene, alkenylene and a covalent bond;

$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

m is an integer from 1 to 3; and n is an integer from 0 to 2, provided that m+n=3;

provided that when m is 1, n is 2, X is 4-sulfo, each $R^1$ is hydrogen and $R^2$ is a covalent bond, then $R^3$ and $R^4$ are not joined to form a 6-methoxycarbonyl-1,1,3-trioxo-1,2-benzisothiazol-2-yl or 1,1,3-trioxo-1,2-benzisothiazol-2-yl group.

65. A method for treating a patient with an inflamnatory disease or autoimmune disease or preventing the onset of an inflammatory or autoimmune disease which method comprises administering to said patient a pharmaceutical composition comprising a pharmaceutically acceptable carrier and an effective inflammatory or autoimmune disease-treating or preventing amount of a compound of formula I:

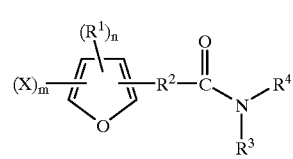

wherein each $R^1$ is independently selected from the group consisting of hydrogen, alkyl, alkenyl, alkynyl, alkaryl, aryl, alkoxy, alkcycloalkyl, cycloalkyl, cycloalkenyl and halo;

$R^2$ is selected from the group consisting of alkylene, alkenylene and a covalent bond;

$R^3$ and $R^4$ are independently selected from the group consisting of hydrogen, alkyl, alkenyl, alkynyl, alkaryl, aryl, alkoxy, alkcycloalkyl, cycloalkyl and cycloalkenyl, provided that $R^3$ and $R^4$ are not both hydrogen; or $R^3$ and $R^4$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

each X is independently selected from the group consisting of —$SO_3Y$ and —$SO_2NR^5R^6$, wherein Y is hydrogen or a pharmaceutically acceptable cation, and $R^5$ and $R^6$ are independently selected from the group consisting of hydrogen, alkyl, alkenyl, alkynyl, alkaryl, aryl, alkoxy, alkcycloalkyl, cycloalkyl and cycloalkenyl; or $R^5$ and $R^6$ can be joined together to form a cycloalkyl ring of from 4 to 10 carbon atoms or a heterocyclic ring of from 4 to 10 atoms having from 1 to 3 heteroatoms selected from the group consisting of oxygen, nitrogen and sulfur;

m is an integer from 1 to 3; and n is an integer from 0 to 2, provided that m+n=3;

provided that when m is 1, n is 2, X is 4-sulfo, each $R^1$ is hydrogen and $R^2$ is a covalent bond, then $R^3$ and $R^4$ are not joined to form a 6-methoxycarbonyl-1,1,3-trioxo-1,2-benzisothiazol-2-yl or 1,1,3-trioxo-1,2-benzisothiazol-2-yl group.

* * * * *